US007718690B2

(12) United States Patent
Ramakrishna et al.

(10) Patent No.: US 7,718,690 B2
(45) Date of Patent: May 18, 2010

(54) N-ARYLSULFONYL-3-AMINOALKOXYINDOLES

(76) Inventors: Venkata Satya Nirogi Ramakrishna, Suven Life Sciences Limited, Serene Chambers, Road No. 7, Banjara Hills, Hyderabad (IN); Vikas Shreekrishna Shirsath, Suven Life Sciences Limited, Serene Chambers, Road No. 7, Banjara Hills, Hyderabad (IN); Rama Sastri Kambhampati, Suven Life Sciences Limited, Serene Chambers, Road No. 7, Banjara Hills, Hyderabad (IN); Venkata Satya Veerabhadra Vadlamudi Rao, Suven Life Sciences Limited, Serene Chambers, Road No. 7, Banjara Hills, Hyderabad (IN); Venkateswarlu Jasti, Suven Life Sciences Limited, Serene Chambers, Road No. 7, Banjara Hills, Hyderabad (IN)

( * ) Notice: Subject to any disclaimer, the term of this patent is extended or adjusted under 35 U.S.C. 154(b) by 0 days.

(21) Appl. No.: 12/349,043

(22) Filed: Jan. 6, 2009

(65) Prior Publication Data
US 2009/0131507 A1 May 21, 2009

Related U.S. Application Data

(62) Division of application No. 10/536,592, filed as application No. PCT/IN03/00370 on Nov. 25, 2003, now Pat. No. 7,507,835.

(30) Foreign Application Priority Data
Nov. 28, 2002 (IN) .................... 883/MAS/2002

(51) Int. Cl.
A61K 31/404 (2006.01)
C07D 209/36 (2006.01)
(52) U.S. Cl. .................... 514/418; 548/469; 548/484; 514/415
(58) Field of Classification Search ............. 548/469, 548/484; 514/415, 418
See application file for complete search history.

(56) References Cited

U.S. PATENT DOCUMENTS

| 3,509,163 | A | 4/1970 | Brandstrom et al. |
| 3,860,608 | A | 1/1975 | Lundt |
| 3,860,609 | A | 1/1975 | Lundt |
| 4,839,377 | A | 6/1989 | Bays |
| 4,855,314 | A | 8/1989 | Oxford |
| 6,465,660 | B1 | 10/2002 | Wierzbicki et al. |
| 7,235,550 | B2 | 6/2007 | Guillaumet et al. |
| 7,507,835 | B2 * | 3/2009 | Ramakrishna et al. ...... 548/484 |

FOREIGN PATENT DOCUMENTS

| DE | 111890 | C | 6/1898 |
| DE | 2024966 | A1 | 12/1970 |
| EP | 0303506 | A2 | 2/1989 |
| EP | 0313397 | A1 | 4/1989 |
| EP | 0354777 | A2 | 2/1990 |
| EP | 0438230 | A2 | 7/1991 |
| EP | 0457701 | A1 | 11/1991 |
| EP | 0497512 | A2 | 8/1992 |
| GB | 1306230 | A | 2/1973 |
| GB | 2035310 | A | 6/1980 |
| JP | 57200362 | A | 12/1982 |
| JP | 1139564 | A | 6/1989 |
| WO | WO-9118897 | A1 | 12/1991 |
| WO | WO-9300086 | A1 | 1/1993 |
| WO | WO-9323396 | A1 | 11/1993 |
| WO | WO-9406769 | A1 | 3/1994 |
| WO | WO-0072815 | A1 | 12/2000 |
| WO | WO-04/000849 | A2 | 12/2003 |

OTHER PUBLICATIONS

Registry No. 123741-97-9, printed from HCAPLUS database on Aug. 16, 2007.
Pruekasaritanont, Thomayant, et al., "Complicating Factors in Safety Testing of Drug . . . ", Toxicology and Applied Pharmacology, 2006, pp. 143-152, vol. 217, Elsevier Inc., USA.
Concise Encyclopedia Chemistry, 1993, Walter de Gruyter Berlin-New York.
Vippagunta, Sudha R., et al., "Crystalline Solids", Advanced Drug Delivery Reviews, 2001, pp. 3-26, vol. 48, Elsevier Science, USA.
Desarbre, et al., Oxidation of Indoles and 1,2-Dihydro-EH-indol-3-ones, Tetrahedron, 1996, pp. 2983-2994, vol. 52, No. 8, Elsevier Science Ltd, GB.
Fuller, R. W., "Biology of Serotoninergic Transmission", Serotoninergic Neuronal Systems, 1982, pp. 221-247, J Wiley & Sons Inc.
Boullin, D.J., et al., International Association for the Scientific Study of Mental Deficiency, "Serotonin in Mental Abnormalities", 1978, pp. 1-340, Wiley, Checester.
Barchas J., et al, "Serotonin and Behavior", 1973, Academic Press, NY.
Gershon, M.D., et al., "The Peripheral Actions of 5-Hydroxytryptamine", 4-Hydroxytryptamine and Enteric Neurons, 1989, pp. 247-273, Oxford, New York.
Saxena, P.R., et al., Journal of Cardiovascular Pharmacology, 1993, pp. 17-34, Supplement 15.
Glennon, et al., Neuroscience and Behavioral Reviews, 1990, pp. 35, vol. 14.
Hoyer, D., et al., Pharmacol. Rev., 1994, pp. 147-203, vol. 46.
Monsma, F. J. Jr., et al., "Molecular Cloning and Expression of Novel Serotonin Receptor . . . ", Mol. Pharmacol, 1993, pp. 320-327, vol. 43.
Ruat, M. et al., Biochem. Biophys. Res. Com., 1993, pp. 269-276, vol. 193.
Roth, et al., J. Pharm. Exp. Therapeut., 1994, pp. 1403-1410, vol. 268.
Sleight, et al., Exp. Opin. Ther. Patents, 1998, pp. 1217-1224, vol. 8.
Bourson, et al., Brit. J. Pharmacol., 1998, pp. 1562-1566, vol. 125.

(Continued)

*Primary Examiner*—Golam M Shameem
(74) *Attorney, Agent, or Firm*—IPHorgan Ltd

(57) ABSTRACT

N-arylsulfonyl-3-aminoalkoxyindoles indole compounds, radioisotopes, stereoisomers, geometric forms, N-oxides, polymorphs and pharmaceutically acceptable salts.

2 Claims, No Drawings

OTHER PUBLICATIONS

Sleight, et al., Brit. J. Pharmacol., 1998, pp. 556-562, vol. 124.
Yoshioka, et al., Life Sciences, 1998, pp. 1473-1477, vol. 17-18.
Withyachumnamkul, et al., Life Sci, 1986, pp. 65, vol. 12.
Barreft, et al., Biol. Signals Recept., 1999, pp. 6-14, vol. 8.
Schoeffter, P. et al., European Journal of Pharmacology, 1993, pp. 251-257, vol. 244.
Bundgard, H., 1985, Design of Prodrugs.
Fieser, Louis F. and Fieser, Mary, "Reagents for Organic Synthesis", 1967-1999, vol. 1, Wiley, New York.
Bellsteins Handbuch der organischen Chemie, 4, Aufl. ed. Springer-Verlag, Berlin.
Greene, T.W., Protective Groups in Organic Synthesis, 1991, John Wiley & Sons, New York.
J. Heterocyclic Chemistry, 1979, pp. 221, vol. 16.
Chem. Pharm. Bull, 1985, pp. 1843, vol. 33.
"Principles of Asymmetric Synthesis", J.E. Baldwin Ed., Tetrahedron series, pp. 311-316, vol. 4.
Jacques, et al., "Enantiomers, Racemates and Resolution", 1981, Wiley Interscience.
Hoyer, D., et al., "Molecular Pharmacology of 5-HT1 and 5-HT2 Recognition Sites in Rat and pig Brain Membranes . . . ", Eur. Jrnl. Pharmacol., 1985, pp. 13-23, vol. 118.
Schoeffter, P., et al., "How Selective is GR 43175? Interactions with Functional . . . ", Naunyn-Schmiedeberg's Arch. Pharmac., 1989, pp. 135-138, vol. 340.
Waeber, C., et al., "Molecular Pharmacology of the 5-HT1D Recognition Sites . . . ", Naunyn-Schmiedeberg's Arch. Pharmac, 1988, pp. 595-601, vol. 337.
Leysen, J. E., et al., "[3H]Ketanserin: A Selective Tritiated Ligand for Serotonin2 Receptor . . . ", Mol. Pharmacol., 1982, pp. 301-314, vol. 21.
Martin, G. R., et al., "Classification Review: Receptors for 5-HT: Current Perspectives on . . . ", Neuropharmacol., 1994, pp. 261-273, vol. 33(3/4).
Shen, Y., "Molecular Cloning and Expression of a 5-hydroxytryptamine7 Serotonin . . . ", J. Biol. Chem., pp. 18200-18204, vol. 268.
Pazos, A., et al., "The Binding of Serotonergic Ligands to the Porcine Choroid Plexus . . . ", Eur. Jrnl. Pharmacol., 1985, pp. 539-546, vol. 106.
Lummis, S. C. R., et al., "Characterization of 5HT3 Receptors in Intact N1E-115 . . . ", Eur. Jrnl. Pharmacol., 1990, pp. 223-227, vol. 189.
Hoyer, D., et al., "Identificationi of Serotonin 5-HT3 Recognition Sites in Membranes . . . ", Mol. Pharmacol., 1988, pp. 303, vol. 33.
Tyers, M.B., "5-Ht3 Receptors and the Therapeutic Potential of 5HT3 Receptor Antagonists", 1991, Therapie., pp. 431-435, vol. 46.
Grossman Kilpatrick, C., et al., Development of a Radioligand Binding Assay for 5HT4 Receptors in Guinea Pig and Rat Brain, Brit. J. Pharmco., 1993, pp. 618-624, vol. 109.
Rees, S., et al., FEBS Letters, 1994, pp. 242-246, vol. 355.
Andersen, K., et al., J. Med. Chem., 1996, pp. 3723-3738, vol. 39.

* cited by examiner

N-ARYLSULFONYL-3-AMINOALKOXYINDOLES

This application is a divisional of U.S. application Ser. No. 10/536,592 filed on May 26, 2005, which is a Sect. 371 National Stage of PCT International Application No. PCT/IN2003/000370, filed on Nov. 25, 2003, claiming priority of Indian Patent Application No. 883/MAS/2002 filed on Nov. 28, 2002, the contents of both applications which are hereby incorporated by reference.

FIELD OF INVENTION

The present invention includes compounds described by general formula (I), its stereoisomers, its radioisotopes, its geometric forms, its N-oxides, its polymorphs, its pharmaceutically acceptable salts, its pharmaceutically acceptable solvates, its useful bio-active metabolites and any suitable combination of the above.

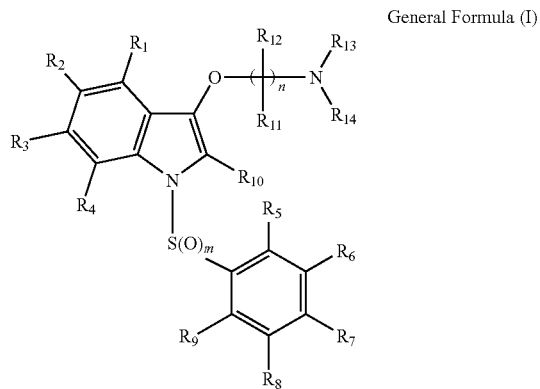

General Formula (I)

Further the present invention also includes the processes for preparing such compounds of the general formula (I), its stereoisomers, its radioisotopes, its geometric forms, its N-oxides, its polymorphs, its pharmaceutically acceptable salts, its pharmaceutically acceptable solvates, its useful bio-active metabolites and also includes any suitable combination of the above.

The invention also describes various methods of administering these compounds of general formula (I), i.e. pharmaceutically acceptable dosage forms compositions and the use of such compounds and compositions in either therapy or diagnosis.

The compounds of the general formula (I) of this invention are 5-HT (Serotonin) ligands e.g. agonists or antagonists. The compounds of the general formula (I) of this invention, by the virtue of its chemical characteristic, could either independently or simultaneously modulate the melatonin receptor i.e. either these compounds are melatonergic ligands e.g. agonists or antagonists, or they interact with both 5-HT and/or Melatonin receptors.

Thus, compounds of general formula (I) of this invention are useful for treating diseases wherein activity of either 5-HT (Serotonin) and/or Melatonin is modulated to obtain the desired therapeutic effect. Specifically, the compounds of this invention are useful in the treatment and/or prophylaxis of conditions such as psychosis, paraphrenia, psychotic depression, mania, schizophrenia, schizophreniform disorders, anxiety, migraine headache, depression, drug addiction, convulsive disorders, personality disorders, hypertension, autism, post-traumatic stress syndrome, alcoholism, panic attacks, obsessive-compulsive disorders, chronobiological abnormalities, circadian rhythms, anxiolytic, osteoporosis, ischemic stroke, lower the risk of SIDS in young infants with low endogenous melatonin levels, reproduction, glaucoma and sleep disorders.

Hence, the compounds of general formula (I) of this invention could also be useful in treating the psychotic, affective, vegetative and psychomotor symptoms of schizophrenia and the extrapyramidal motor side effects of other antipsychotic drugs; neurodegenerative disorders like Alzheimer's disease, Parkinson's and Huntington's chorea and chemotherapy-induced vomiting; and in modulation of eating behavior and thus are useful in reducing the morbidity and mortality associated with excess weight.

BACKGROUND OF THE INVENTION

Many diseases of the central nervous system are influenced by the adrenergic, the dopaminergic and the serotoninergic neurotransmitter systems. Serotonin has been implicated in numerous diseases and conditions, which originate from central nervous system. The list includes diseases and conditions related to sleeping, eating, perceiving pain, controlling body temperature, controlling blood pressure, depression, anxiety, schizophrenia and other bodily states. (References: Fuller, R. W., Drugs Acting on Serotoninergic Neuronal Systems, in "Biology of Serotoninergic Transmission", ed. by Osborne N. N., J Wiley & Sons Inc. (1982), 221-247; Boullin D. J., et. al., in "Serotonin in Mental Abnormalities", International Association for The Scientific Study of Mental Deficiency, Wiley, Checester, 1978, pp. 1-340; Barchas J. et. al., in "Serotonin and Behavior", Academic Press, NY (1973)). Serotonin also plays an important role in the peripheral systems, such as the gastrointestinal system, where it has been found to mediate a variety of contractile, secretory and electrophysiologic effects.

Due to the broad distribution of serotonin within the body, there is a lot of interest and use, in the drugs that affect serotoninergic systems. Particularly, preferred are the compounds which have receptor-specific agonism and/or antagonism for the treatment of a wide range of disorders, including anxiety, depression, hypertension, migraine, obesity, compulsive disorders, schizophrenia, autism, certain other neurodegenerative disorders like Alzheimer, Parkinson, Huntington's chorea and chemotherapy-induced vomiting (References: Gershon M. D. et. al., 5-Hydroxytryptamine and enteric neurons. In: *The Peripheral Actions of 5-Hydroxytryptamine*, edited by J. R. Fozard. New York: Oxford, 1989, p. 247-273; Saxena P. R., et. al., *Journal of Cardiovascular Pharmacology* (1993), supplement 15, p. 17-34).

The major classes of serotonin receptors ($5\text{-}HT_{1\text{-}7}$) contain fourteen to eighteen separate receptors that have been formally classified (References: Glennon et al, Neuroscience and Behavioral Reviews (1990), 14, 35; and Hoyer D. et al, Pharmacol. Rev. (1994), 46, 157-203). Recently discovered information regarding sub-type identity, distribution, structure and function suggests that it is possible to identify novel, sub-type specific agents having improved therapeutic profiles with lesser side effects. The $5\text{-}HT_6$ receptor was identified in 1993 (References: Monsma et al, Mol. Pharmacol. (1993), 43, 320-327; and Ruat M. et al, Biochem. Biophys. Res. Com. (1993), 193, 269-276). Several antidepressants and atypical antipsychotics bind to the $5\text{-}HT_6$ receptor with high affinity and this binding may be a factor in their profile of activities (References: Roth et al, J. Pharm. Exp. Therapeut. (1994), 268, 1403-1410; Sleight et al, Exp. Opin. Ther. Patents (1998), 8, 1217-1224; Bourson et al, Brit. J. Pharmacol.

(1998), 125, 1562-1566; Boess et al, Mol. Pharmacol., 1998, 54, 577-583; Sleight et al, Brit. J. Pharmacol. (1998), 124, 556-562). In addition, 5-HT$_6$ receptor has been linked to generalized stress and anxiety states (Reference: Yoshioka et al, Life Sciences (1998), 17/18, 1473-1477). Together these studies and observations suggest that the compound, which antagonizes 5-HT$_6$ receptors, will be useful in treating various disorders of the central nervous system.

There is very strong evidence that Melatonin is important for the regulation of a variety of neural and endocrine functions, especially those that exhibit circadian and circannual rhythmicity. Great interest therefore lies in the possibility of making available to the clinician melatonin analogues that are metabolically more stable and have an agonist or antagonist character and of which the therapeutic effect may be expected to be superior to that of the hormone itself. PCT patent application WO 00/72815 and U.S. Pat. No. 6,465,660B1 gives extensive literature on studies with Melatonin and potential therapeutic application of various ligands reported till date.

Those various effects are exerted via the intermediary of specific Melatonin receptors. Molecular biology studies have demonstrated the existence of a number of receptor sub-types that are capable of binding that hormone (Trends Pharmacol. Sci., 1995, 16, p. 50; WO 97 04094). Melatonin acts on the CNS to affect neural mechanisms through receptors located in the brain. Additionally, a number of studies indicate the existence of direct effects of Melatonin in peripheral organs via peripheral melatonin receptors. Melatonin receptors are present in the heart, lungs, prostate gland, gonads, white blood cells, retina, pituitary, thyroid, kidney, gut and blood vessels (Withyachumnamkul et al., Life Sci, 12 65, 1986). Three Melatonin receptor subtypes have been identified so far MT-1, MT-2 and Mel 1 c (Barreft et al., Biol. Signals Recept., 1999, 8: 6-14).

There is evidence suggesting both Melatonin agonists and antagonists would be of potential therapeutic use for a variety of maladies and conditions. PCT application WO 00/72815 and U.S. Pat. No. 6,465,660B1 discuss in depth applications and use of such compounds and details of which are incorporated herein by reference. Also U.S. Pat. No. 6,465,660 and U.S. patent application publication number U.S. 2003/0105087 discuss some tricyclic indole and tricyclic azaindole derivatives having very valuable pharmacological characteristics in respect of melatoninergic receptors.

U.S. Pat. No. 4,839,377 and U.S. Pat. No. 4,855,314 refers to 5-substituted 3-aminoalkyl indoles. The compounds are said to be useful for the treatment of migraine.

British Patent 2,035,310 refers to 3-aminoalkyl-1H-indole-5-thioamides and carboxamides. The compounds are said to be useful in treating hypertension, Raymond's disease and migraine.

European Patent Publication 303,506 refers to 3-polyhydropyridyl-5-substituted-1H-indoles. The compounds are said to have 5-HT$_1$ receptor agonists and vasoconstrictor activity and to be useful in treating migraine. European Patent Publication 354,777 refers to N-piperidinylindolylethyl-alkane sulfonamide derivatives. The compounds are said to be 5-HT$_1$ receptor agonists and have vasoconstrictor activity and are useful in treating cephalic pain.

European Patent Publication 438,230, refers to indole-substituted five-membered heteroaromatic compounds. The compounds are said to have "5-HT$_1$-like" receptor agonist activity and to be useful in the treatment of migraine and other disorders for which a selective agonist of these receptors is indicated.

European Patent Publication 313,397 refers to 5-heterocyclic indole derivatives. The compounds are said to have exceptional properties for the treatment and prophylaxis of migraine, cluster headache and headache associated with vascular disorders. These compounds are also said to have exceptional "5-HT$_1$-like" receptor agonism.

International Patent Publication WO 91/18897 refers to 5-heterocyclic indole derivatives. The compounds are said to have exceptional properties for the treatment and prophylaxis of migraine, cluster headache, and headache associated with vascular disorders. These compounds are also said to have exceptional "5-HT$_1$-like" receptor agonism.

European Patent Publication 457,701 refers to aryloxy amine derivatives as having high affinity for 5-HT$_{1D}$ serotonin receptors. These compounds are said to be useful for treating diseases related to serotonin receptor dysfunction, for example, migraine.

European Patent Publication 497,512 A2, refers to a class of imidazole, triazole and tetrazole derivatives that are selective agonists for "5-HT$_1$-like" receptors. These compounds are said to be useful for treating migraine and associated disorders.

International Patent Publication WO 93/00086 describes a series of tetrahydrocarbazole derivatives, as 5-HT$_1$ receptor agonists, useful for the treatment of migraine and related conditions.

International Patent Publication WO 93/23396, refers to fused imidazole and triazole derivatives as 5-HT$_1$ receptor agonists, for the treatment of migraine and other disorders.

Schoeffter P. et al. refers to methyl 4-{4-[4-(1,1,3-trioxo-2H-1,2-benzoisothiazol-2-yl)butyl]-1-piperazinyl}1H-indole-3-carboxylate as a selective antagonist for the 5-HT$_{1A}$ receptor in their paper "SDZ216-525, a selective and potent 5-HT$_{1A}$ receptor antagonist", European Journal of Pharmacology, 244, 251-257 (1993).

International Patent Publication WO 94/06769, refers to 2-substituted-4-piperazine-benzothiophene derivatives that are serotonin 5-HT$_{1A}$ and 5-HT$_{1D}$ receptor agents useful in the treatment of anxiety, depression, migraine, stroke, angina and hypertension.

SUMMARY OF THE INVENTION

The present invention relates to compounds of general formula (I), its stereoisomers, its radioisotopes, its geometric forms, its N-oxide, its polymorphs, its pharmaceutically acceptable salts, its pharmaceutically acceptable solvates, its useful bio-active metabolites and any suitable combination of the above.

The compounds of general formula (I) are as follows,

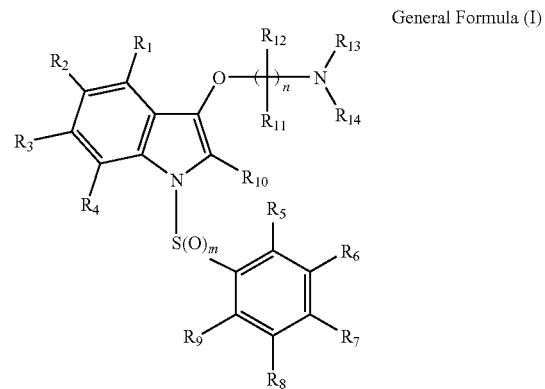

General Formula (I)

wherein $R_1$, $R_2$, $R_3$, $R_4$, $R_5$, $R_6$, $R_7$, $R_8$, $R_9$, $R_{11}$ and $R_{12}$ may be same or different, and represent hydrogen, halogen, perhaloalkyl, hydroxy, thio, amino, nitro, cyano, formyl, amidino, guanidino, substituted or unsubstituted groups selected from linear or branched $(C_1$-$C_{12})$alkyl, $(C_2$-$C_{12})$alkenyl, $(C_2$-$C_{12})$alkynyl, $(C_3$-$C_7)$cycloalkyl, $(C_3$-$C_7)$cycloalkenyl, bicycloalkyl, bicycloalkenyl, $(C_1$-$C_{12})$alkoxy, cyclo$(C_3$-$C_7)$ alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from O, N, S and combinations of double bond and heteroatoms; or $R_{11}$ and $R_{12}$ together with carbon atoms to which they are attached may form a three to a six membered ring, optionally containing one or more double bonds and optionally containing one or more heteroatoms selected from O, N, S and combinations of double bond and heteroatoms.

$R_{10}$ represents hydrogen, halogen, perhaloalkyl, substituted or unsubstituted groups selected from linear or branched $(C_1$-$C_3)$alkyl and aryl.

$R_{13}$ and $R_{14}$ represents hydrogen, alkyl, aryl, aralkyl or together with nitrogen atom form a cyclic three to seven membered ring, optionally, $R_{11}$ and $R_{13}$ together may form a part of cyclic structure along with the intervening nitrogen and carbon atoms; the heterocycle may have either one, two or three double bonds; optionally it may also contain one to three heteroatom selected from the group of oxygen, nitrogen and sulfur, and includes ring fused with any carbocyclic or heterocyclic ring, which can be saturated or unsaturated.

"n" is an integer ranging from 1 to 8, preferably 1 to 4, wherein the carbon chains which "n" represents may be either linear or branched.

"m" is an integer ranging from 0 to 2 preferably m is 1 or 2; along with the proviso that whenever m=2 and each of $R_5$, $R_6$, $R_7$, $R_8$ and $R_9$ are hydrogens then all of $R_1$, $R_2$, $R_3$, $R_4$ and $R_{10}$, together are never hydrogens.

Partial List of Such Compounds of General Formula (I) is as Follows:

[2-(1-(Benzenesulfonyl)-1H-indol-3-yloxy)ethyl]dimethylamine;
[2-(1-(4'-Isopropylbenzenesulfonyl)-1H-indol-3-yloxy)ethyl]dimethylamine;
[2-(1-(2'-Bromo-4'-methoxybenzenesulfonyl)-1H-indol-3-yloxy)ethyl]dimethylamine;
[2-(1-(2',4'-Dimethoxybenzenesulfonyl)-1H-indol-3-yloxy)ethyl]dimethylamine;
[2-(1-(4'-Bromobenzenesulfonyl)-1H-indol-3-yloxy)ethyl]dimethylamine;
[2-(1-(2'-Bromo-4'-Methylbenzenesulfonyl)-1H-indol-3-yloxy)ethyl]dimethylamine
[2-(1-(2'-Bromobenzenesulfonyl)-1H-indol-3-yloxy)ethyl]dimethylamine;
[2-(1-(4'-Fluorobenzenesulfonyl)-1H-indol-3-yloxy)ethyl]dimethylamine;
[2-(1-(4'-Chlorobenzenesulfonyl)-1H-indol-3-yloxy)ethyl]dimethylamine;
[2-(1-(4'-Methylbenzenesulfonyl)-1H-indol-3-yloxy)ethyl]dimethylamine;
[2-(1-(Benzenesulfonyl)-2-phenyl-1H-indol-3-yloxy)ethyl]dimethylamine;
[2-(1-(4'-Isopropylbenzenesulfonyl)-2-phenyl-1H-indol-3-yloxy)ethyl]dimethylamine;
[2-(1-(2'-Bromo-4'-methoxybenzenesulfonyl)-2-phenyl-1H-indol-3-yloxy)ethyl]dimethylamine;
[2-(1-(2',4'-Dimethoxybenzenesulfonyl)-2-phenyl-1H-indol-3-yloxy)ethyl]dimethylamine;
[2-(1-(4'-Bromobenzenesulfonyl)-2-phenyl-1H-indol-3-yloxy)ethyl]dimethylamine
[2-(1-(2'-Bromo-4'-Methylbenzenesulfonyl)-2-phenyl-1H-indol-3-yloxy)ethyl]dimethylamine;
[2-(1-(2'-Bromobenzenesulfonyl)-2-phenyl-1H-indol-3-yloxy)ethyl]dimethylamine
[2-(1-(4'-Fluorobenzenesulfonyl)-2-phenyl-1H-indol-3-yloxy)ethyl]dimethylamine;
[2-(1-(4'-Chlorobenzenesulfonyl)-2-phenyl-1H-indol-3-yloxy)ethyl]dimethylamine
[2-(1-(4'-Methylbenzenesulfonyl)-2-phenyl-1H-indol-3-yloxy)ethyl]dimethylamine
[2-(1-(Benzenesulfonyl)-2-methyl-1H-indol-3-yloxy)ethyl]dimethylamine;
[2-(1-(4'-Isopropylbenzenesulfonyl)-2-methyl-1H-indol-3-yloxy)ethyl]dimethylamine;
[2-(1-(2'-Bromo-4'-methoxybenzenesulfonyl)-2-methyl-1H-indol-3-yloxy)ethyl]dimethylamine;
[2-(1-(2',4'-Dimethoxybenzenesulfonyl)-2-methyl-1H-indol-3-yloxy)ethyl]dimethylamine;
[2-(1-(4'-Bromobenzenesulfonyl)-2-methyl-1H-indol-3-yloxy)ethyl]dimethylamine;
[2-(1-(2'-Bromo-4'-Methylbenzenesulfonyl)-2-methyl-1H-indol-3-yloxy)ethyl]dimethylamine;
[2-(1-(2'-Bromobenzenesulfonyl)-2-methyl-1H-indol-3-yloxy)ethyl]dimethylamine;
[2-(1-(4'-Fluorobenzenesulfonyl)-2-methyl-1H-indol-3-yloxy)ethyl]dimethylamine;
[2-(1-(4'-Chlorobenzenesulfonyl)-2-methyl-1H-indol-3-yloxy)ethyl]dimethylamine;
[2-(1-(4'-Methylbenzenesulfonyl)-2-methyl-1H-indol-3-yloxy)ethyl]dimethylamine;
[2-(1-(Benzenesulfonyl)-5-bromo-1H-indol-3-yloxy)ethyl]dimethylamine;
[2-(1-(4'-Isopropylbenzenesulfonyl)-5-bromo-1H-indol-3-yloxy)ethyl]dimethylamine;
[2-(1-(2'-Bromo-4'-methoxybenzenesulfonyl)-5-bromo-1H-indol-3-yloxy)ethyl]dimethylamine;
[2-(1-(2',4'-Dimethoxybenzenesulfonyl)-5-bromo-1H-indol-3-yloxy)ethyl]dimethylamine;
[2-(1-(4'-Bromobenzenesulfonyl)-5-bromo-1H-indol-3-yloxy)ethyl]dimethylamine
[2-(1-(2'-Bromo-4'-Methylbenzenesulfonyl)-5-bromo-1H-indol-3-yloxy)ethyl]dimethylamine;
[2-(1-(2'-Bromobenzenesulfonyl)-5-bromo-1H-indol-3-yloxy)ethyl]dimethylamine
[2-(1-(4'-Fluorobenzenesulfonyl)-5-bromo-1H-indol-3-yloxy)ethyl]dimethylamine;
[2-(1-(4'-Chlorobenzenesulfonyl)-5-bromo-1H-indol-3-yloxy)ethyl]dimethylamine

[2-(1-(4'-Methylbenzenesulfonyl)-5-bromo-1H-indol-3-yloxy)ethyl]dimethylamine
[2-(1-(Benzenesulfonyl)-5-bromo-2-phenyl-1H-indol-3-yloxy)ethyl]dimethylamine;
[2-(1-(4'-Isopropylbenzenesulfonyl)-5-bromo-2-phenyl-1H-indol-3-yloxy)ethyl]dimethylamine;
[2-(1-(2'-Bromo-4'-methoxybenzenesulfonyl)-5-bromo-2-phenyl-1H-indol-3-yloxy)ethyl]dimethylamine;
[2-(1-(2',4'-Dimethoxybenzenesulfonyl)-5-bromo-2-phenyl-1H-indol-3-yloxy)ethyl]dimethylamine;
[2-(1-(4'-Bromobenzenesulfonyl)-5-bromo-2-phenyl-1H-indol-3-yloxy)ethyl]dimethylamine;
[2-(1-(2'-Bromo-4'-Methylbenzenesulfonyl)-5-bromo-2-phenyl-1H-indol-3-yloxy)ethyl]dimethylamine;
[2-(1-(2'-Bromobenzenesulfonyl)-5-bromo-2-phenyl-1H-indol-3-yloxy)ethyl]dimethylamine;
[2-(1-(4'-Fluorobenzenesulfonyl)-5-bromo-2-phenyl-1H-indol-3-yloxy)ethyl]dimethylamine;
[2-(1-(4'-Chlorobenzenesulfonyl)-5-bromo-2-phenyl-1H-indol-3-yloxy)ethyl]dimethylamine;
[2-(1-(4'-Methylbenzenesulfonyl)-5-bromo-2-phenyl-1H-indol-3-yloxy)ethyl]dimethylamine;
[2-(1-(Benzenesulfonyl)-5-bromo-2-methyl-1H-indol-3-yloxy)ethyl]dimethylamine
[2-(1-(4'-Isopropylbenzenesulfonyl)-5-bromo-2-methyl-1H-indol-3-yloxy)ethyl]dimethylamine;
[2-(1-(2'-Bromo-4'-methoxybenzenesulfonyl)-5-bromo-2-methyl-1H-indol-3-yloxy)ethyl]dimethylamine;
[2-(1-(2',4'-Dimethoxybenzenesulfonyl)-5-bromo-2-methyl-1H-indol-3-yloxy)ethyl]dimethylamine;
[2-(1-(4'-Bromobenzenesulfonyl)-5-bromo-2-methyl-1H-indol-3-yloxy)ethyl]dimethylamine;
[2-(1-(2'-Bromo-4'-Methylbenzenesulfonyl)-5-bromo-2-methyl-1H-indol-3-yloxy)ethyl]dimethylamine;
[2-(1-(2'-Bromobenzenesulfonyl)-5-bromo-2-methyl-1H-indol-3-yloxy)ethyl]dimethylamine;
[2-(1-(4'-Fluorobenzenesulfonyl)-5-bromo-2-methyl-1H-indol-3-yloxy)ethyl]dimethylamine;
[2-(1-(4'-Chlorobenzenesulfonyl)-5-bromo-2-methyl-1H-indol-3-yloxy)ethyl]dimethylamine;
[2-(1-(4'-Methylbenzenesulfonyl)-5-bromo-2-methyl-1H-indol-3-yloxy)ethyl]dimethylamine;
[2-(1-(Benzenesulfonyl)-6-chloro-1H-indol-3-yloxy)ethyl]dimethylamine;
[2-(1-(4'-Isopropylbenzenesulfonyl)-6-chloro-1H-indol-3-yloxy)ethyl]dimethylamine;
[2-(1-(2'-Bromo-4'-methoxybenzenesulfonyl)-6-chloro-1H-indol-3-yloxy)ethyl]dimethylamine;
[2-(1-(2',4'-Dimethoxybenzenesulfonyl)-6-chloro-1H-indol-3-yloxy)ethyl]dimethylamine;
[2-(1-(4'-Bromobenzenesulfonyl)-6-chloro-1H-indol-3-yloxy)ethyl]dimethylamine
[2-(1-(2'-Bromo-4'-Methylbenzenesulfonyl)-6-chloro-1H-indol-3-yloxy)ethyl]dimethylamine;
[2-(1-(2'-Bromobenzenesulfonyl)-6-chloro-1H-indol-3-yloxy)ethyl]dimethylamine
[2-(1-(4'-Fluorobenzenesulfonyl)-6-chloro-1H-indol-3-yloxy)ethyl]dimethylamine;
[2-(1-(4'-Chlorobenzenesulfonyl)-6-chloro-1H-indol-3-yloxy)ethyl]dimethylamine;
[2-(1-(4'-Methylbenzenesulfonyl)-6-chloro-1H-indol-3-yloxy)ethyl]dimethylamine;
[2-(1-(Benzenesulfonyl)-6-chloro-2-phenyl-1H-indol-3-yloxy)ethyl]dimethylamine
[2-(1-(4'-Isopropylbenzenesulfonyl)-6-chloro-2-phenyl-1H-indol-3-yloxy)ethyl]dimethylamine;
[2-(1-4'-Bromo-4'-methoxybenzenesulfonyl)-6-chloro-2-phenyl-1H-indol-3-yloxy)ethyl]dimethylamine;
[2-(1-(2',4'-Dimethoxybenzenesulfonyl)-6-chloro-2-phenyl-1H-indol-3-yloxy)ethyl]dimethylamine;
[2-(1-(4'-Bromobenzenesulfonyl)-6-chloro-2-phenyl-1H-indol-3-yloxy)ethyl]dimethylamine;
[2-(1-(2'-Bromo-4'-Methylbenzenesulfonyl)-6-chloro-2-phenyl-1H-indol-3-yloxy)ethyl]dimethylamine;
[2-(1-(2'-Bromobenzenesulfonyl)-6-chloro-2-phenyl-1H-indol-3-yloxy)ethyl]dimethylamine;
[2-(1-(4'-Fluorobenzenesulfonyl)-6-chloro-2-phenyl-1H-indol-3-yloxy)ethyl]dimethylamine;
[2-(1-(4'-Chlorobenzenesulfonyl)-6-chloro-2-phenyl-1H-indol-3-yloxy)ethyl]dimethylamine;
[2-(1-(4'-Methylbenzenesulfonyl)-6-chloro-2-phenyl-1H-indol-3-yloxy)ethyl]dimethylamine;
[2-(1-(Benzenesulfonyl)-6-chloro-2-methyl-1H-indol-3-yloxy)ethyl]dimethylamine
[2-(1-(4'-Isopropylbenzenesulfonyl)-6-chloro-2-methyl-1H-indol-3-yloxy)ethyl]dimethylamine;
[2-(1-(2'-Bromo-4'-methoxybenzenesulfonyl)-6-chloro-2-methyl-1H-indol-3-yloxy)ethyl]dimethylamine;
[2-(1-(2',4'-Dimethoxybenzenesulfonyl)-6-chloro-2-methyl-1H-indol-3-yloxy)ethyl]dimethylamine;
[2-(1-(4'-Bromobenzenesulfonyl)-6-chloro-2-methyl-1H-indol-3-yloxy)ethyl]dimethylamine;
[2-(1-(2'-Bromo-4'-Methylbenzenesulfonyl)-6-chloro-2-methyl-1H-indol-3-yloxy)ethyl]dimethylamine;
[2-(1-(2'-Bromobenzenesulfonyl)-6-chloro-2-methyl-1H-indol-3-yloxy)ethyl]dimethylamine;
[2-(1-(4'-Fluorobenzenesulfonyl)-6-chloro-2-methyl-1H-indol-3-yloxy)ethyl]dimethylamine;
[2-(1-(4'-Chlorobenzenesulfonyl)-6-chloro-2-methyl-1H-indol-3-yloxy)ethyl]dimethylamine;
[2-(1-(4'-Methylbenzenesulfonyl)-6-chloro-2-methyl-1H-indol-3-yloxy)ethyl]dimethylamine;
[2-(1-(Benzenesulfonyl)-5-chloro-1H-indol-3-yloxy)ethyl]dimethylamine;
[2-(1-(4'-Isopropylbenzenesulfonyl)-5-chloro-1H-indol-3-yloxy)ethyl]dimethylamine;
[2-(1-(2'-Bromo-4'-methoxybenzenesulfonyl)-5-chloro-1H-indol-3-yloxy)ethyl]dimethylamine;
[2-(1-(2',4'-Dimethoxybenzenesulfonyl)-5-chloro-1H-indol-3-yloxy)ethyl]dimethylamine;
[2-(1-(4'-Bromobenzenesulfonyl)-5-chloro-1H-indol-3-yloxy)ethyl]dimethylamine
[2-(1-(2'-Bromo-4'-Methylbenzenesulfonyl)-5-chloro-1H-indol-3-yloxy)ethyl]dimethylamine;
[2-(1-(2-Bromobenzenesulfonyl)-5-chloro-1H-indol-3-yloxy)ethyl]dimethylamine
[2-(1-(4'-Fluorobenzenesulfonyl)-5-chloro-1H-indol-3-yloxy)ethyl]dimethylamine
[2-(1-(4'-Chlorobenzenesulfonyl)-5-chloro-1H-indol-3-yloxy)ethyl]dimethylamine
[2-(1-(4'-Methylbenzenesulfonyl)-5-chloro-1H-indol-3-yloxy)ethyl]dimethylamine
[2-(1-(Benzenesulfonyl)-5-chloro-2-phenyl-1H-indol-3-yloxy)ethyl]dimethylamine
[2-(1-(4'-Isopropylbenzenesulfonyl)-5-chloro-2-phenyl-1H-indol-3-yloxy)ethyl]dimethylamine;
[2-(1-(2'-Bromo-4-methoxybenzenesulfonyl)-5-chloro-2-phenyl-1H-indol-3-yloxy)ethyl]dimethylamine;
[2-(1-(2',4'-Dimethoxybenzenesulfonyl)-5-chloro-2-phenyl-1H-indol-3-yloxy)ethyl]dimethylamine;
[2-(1-(4'-Bromobenzenesulfonyl)-5-chloro-2-phenyl-1H-indol-3-yloxy)ethyl]dimethylamine;

[2-(1-(2'-Bromo-4'-Methylbenzenesulfonyl)-5-chloro-2-phenyl-1H-indol-3-yloxy)ethyl]dimethylamine;
[2-(1-(2'-Bromobenzenesulfonyl)-5-chloro-2-phenyl-1H-indol-3-yloxy)ethyl]dimethylamine;
[2-(1-(4'-Fluorobenzenesulfonyl)-5-chloro-2-phenyl-1H-indol-3-yloxy)ethyl]dimethylamine;
[2-(1-(4'-Chlorobenzenesulfonyl)-5-chloro-2-phenyl-1H-indol-3-yloxy)ethyl]dimethylamine;
[2-(1-(4-Methylbenzenesulfonyl)-5-chloro-2-phenyl-1H-indol-3-yloxy)ethyl]dimethylamine;
[2-(1-(Benzenesulfonyl)-5-chloro-2-methyl-1H-indol-3-yloxy)ethyl]dimethylamine
[2-(1-(4'-Isopropylbenzenesulfonyl)-5-chloro-2-methyl-1H-indol-3-yloxy)ethyl]dimethylamine;
[2-(1-(2'-Bromo-4'-methoxybenzenesulfonyl)-5-chloro-2-methyl-1H-indol-3-yloxy)ethyl]dimethylamine;
[2-(1-(2',4'-Dimethoxybenzenesulfonyl)-5-chloro-2-methyl-1H-indol-3-yloxy)ethyl]dimethylamine;
[2-(1-(4'-Bromobenzenesulfonyl)-5-chloro-2-methyl-1H-indol-3-yloxy)ethyl]dimethylamine;
[2-(1-(2'-Bromo-4'-Methylbenzenesulfonyl)-5-chloro-2-methyl-1H-indol-3-yloxy)ethyl]dimethylamine;
[2-(1-(2'-Bromobenzenesulfonyl)-5-chloro-2-methyl-1H-indol-3-yloxy)ethyl]dimethylamine;
[2-(1-(4'-Fluorobenzenesulfonyl)-5-chloro-2-methyl-1H-indol-3-yloxy)ethyl]dimethylamine;
[2-(1-(4-Chlorobenzenesulfonyl)-5-chloro-2-methyl-1H-indol-3-yloxy)ethyl]dimethylamine;
[2-(1-(4'-Methylbenzenesulfonyl)-5-chloro-2-methyl-1H-indol-3-yloxy)ethyl]dimethylamine;
[2-(1-(Benzenesulfonyl)-5,7-dichloro-1H-indol-3-yloxy)ethyl]dimethylamine;
[2-(1-(4'-Isopropylbenzenesulfonyl)-5,7-dichloro-1H-indol-3-yloxy)ethyl]dimethylamine;
[2-(1-(2'-Bromo-4'-methoxybenzenesulfonyl)-5,7-dichloro-1H-indol-3-yloxy)ethyl]dimethylamine;
[2-(1-(2',4'-Dimethoxybenzenesulfonyl)-5,7-dichloro-1H-indol-3-yloxy)ethyl]dimethylamine;
[2-(1-(4'-Bromobenzenesulfonyl)-5,7-dichloro-1H-indol-3-yloxy)ethyl]dimethylamine;
[2-(1-(2'-Bromo-4'-Methylbenzenesulfonyl)-5,7-dichloro-1H-indol-3-yloxy)ethyl]dimethylamine;
[2-(1-(2'-Bromobenzenesulfonyl)-5,7-dichloro-1H-indol-3-yloxy)ethyl]dimethylamine;
[2-(1-(4'-Fluorobenzenesulfonyl)-5,7-dichloro-1H-indol-3-yloxy)ethyl]dimethylamine;
[2-(1-(4'-Chlorobenzenesulfonyl)-5,7-dichloro-1H-indol-3-yloxy)ethyl]dimethylamine;
[2-(1-(4'-Methylbenzenesulfonyl)-5,7-dichloro-1H-indol-3-yloxy)ethyl]dimethylamine;
[2-(1-(Benzenesulfonyl)-5,7-dichloro-2-phenyl-1H-indol-3-yloxy)ethyl]dimethylamine;
[2-(1-(4'-Isopropylbenzenesulfonyl)-5,7-dichloro-2-phenyl-1H-indol-3-yloxy)ethyl]dimethylamine;
[2-(1-(2'-Bromo-4'-methoxybenzenesulfonyl)-5,7-dichloro-2-phenyl-1H-indol-3-yloxy)ethyl]dimethylamine;
[2-(1-(2',4'-Dimethoxybenzenesulfonyl)-5,7-dichloro-2-phenyl-1H-indol-3-yloxy)ethyl]dimethylamine;
[2-(1-(4'-Bromobenzenesulfonyl)-5,7-dichloro-2-phenyl-1H-indol-3-yloxy)ethyl]dimethylamine;
[2-(1-(2'-Bromo-4'-Methylbenzenesulfonyl)-5,7-dichloro-2-phenyl-1H-indol-3-yloxy)ethyl]dimethylamine;
[2-(1-(2'-Bromobenzenesulfonyl)-5,7-dichloro-2-phenyl-1H-indol-3-yloxy)ethyl]dimethylamine;
[2-(1-(4'-Fluorobenzenesulfonyl)-5,7-dichloro-2-phenyl-1H-indol-3-yloxy)ethyl]dimethylamine;
[2-(1-(4-Chlorobenzenesulfonyl)-5,7-dichloro-2-phenyl-1H-indol-3-yloxy)ethyl]dimethylamine;
[2-(1-(4'-Methylbenzenesulfonyl)-5,7-dichloro-2-phenyl-1H-indol-3-yloxy)ethyl]dimethylamine;
[2-(1-(Benzenesulfonyl)-5,7-dichloro-2-methyl-1H-indol-3-yloxy)ethyl]dimethylamine;
[2-(1-(4'-Isopropylbenzenesulfonyl)-5,7-dichloro-2-methyl-1H-indol-3-yloxy)ethyl]dimethylamine;
[2-(1-(2'-Bromo-4'-methoxybenzenesulfonyl)-5,7-dichloro-2-methyl-1H-indol-3-yloxy)ethyl]dimethylamine;
[2-(1-(2',4'-Dimethoxybenzenesulfonyl)-5,7-dichloro-2-methyl-1H-indol-3-yloxy)ethyl]dimethylamine;
[2-(1-(4'-Bromobenzenesulfonyl)-5,7-dichloro-2-methyl-1H-indol-3-yloxy)ethyl]dimethylamine;
[2-(1-(2'-Bromo,4'-Methylbenzenesulfonyl)-5,7-dichloro-2-methyl-1H-indol-3-yloxy) ethyl]dimethylamine;
[2-(1-(2'-Bromobenzenesulfonyl)-5,7-dichloro-2-methyl-1H-indol-3-yloxy)ethyl]dimethylamine;
[2-(1-(4'-Fluorobenzenesulfonyl)-5,7-dichloro-2-methyl-1H-indol-3-yloxy)ethyl]dimethylamine;
[2-(1-(4'-Chlorobenzenesulfonyl)-5,7-dichloro-2-methyl-1H-indol-3-yloxy)ethyl]dimethylamine;
[2-(1-(4'-Methylbenzenesulfonyl)-5,7-dichloro-2-methyl-1H-indol-3-yloxy)ethyl]dimethylamine;
[2-(1-(Benzenesulfonyl)-5,7-dibromo-1H-indol-3-yloxy)ethyl]dimethylamine
[2-(1-(4'-Isopropylbenzenesulfonyl)-5,7-dibromo-1H-indol-3-yloxy)ethyl]dimethylamine;
[2-(1-(2'-Bromo-4'-methoxybenzenesulfonyl)-5,7-dibromo-1H-indol-3-yloxy)ethyl]dimethylamine;
[2-(1-(2',4'-Dimethoxybenzenesulfonyl)-5,7-dibromo-1H-indol-3-yloxy)ethyl]dimethylamine;
[2-(1-(4'-Bromobenzenesulfonyl)-5,7-dibromo-1H-indol-3-yloxy)ethyl]dimethylamine;
[2-(1-(2'-Bromo-4'-Methylbenzenesulfonyl)-5,7-dibromo-1H-indol-3-yloxy)ethyl]dimethylamine;
[2-(1-(2'-Bromobenzenesulfonyl)-5,7-dibromo-1H-indol-3-yloxy)ethyl]dimethylamine;
[2-(1-(4'-Fluorobenzenesulfonyl)-5,7-dibromo-1H-indol-3-yloxy)ethyl]dimethylamine;
[2-(1-(4'-Chlorobenzenesulfonyl)-5,7-dibromo-1H-indol-3-yloxy)ethyl]dimethylamine;
[2-(1-(4'-Methylbenzenesulfonyl)-5,7-dibromo-1H-indol-3-yloxy)ethyl]dimethylamine;
[2-(1-(Benzenesulfonyl)-5,7-dibromo-2-phenyl-1H-indol-3-yloxy)ethyl]dimethylamine;
[2-(1-(4'-Isopropylbenzenesulfonyl)-5,7-dibromo-2-phenyl-1H-indol-3-yloxy)ethyl]dimethylamine;
[2-(1-(2'-Bromo-4'-methoxybenzenesulfonyl)-5,7-dibromo-2-phenyl-1H-indol-3-yloxy)ethyl]dimethylamine;
[2-(1-(2',4'-Dimethoxybenzenesulfonyl)-5,7-dibromo-2-phenyl-1H-indol-3-yloxy)ethyl]dimethylamine;
[2-(1-(4'-Bromobenzenesulfonyl)-5,7-dibromo-2-phenyl-1H-indol-3-yloxy)ethyl]dimethylamine;
[2-(1-(2'-Bromo-4-Methylbenzenesulfonyl)-5,7-dibromo-2-phenyl-1H-indol-3-yloxy)ethyl]dimethylamine;
[2-(1-(2'-Bromobenzenesulfonyl)-5,7-dibromo-2-phenyl-1H-indol-3-yloxy)ethyl]dimethylamine;
[2-(1-(4'-Fluorobenzenesulfonyl)-5,7-dibromo-2-phenyl-1H-indol-3-yloxy)ethyl]dimethylamine;
[2-(1-(4'-Chlorobenzenesulfonyl)-5,7-dibromo-2-phenyl-1H-indol-3-yloxy)ethyl]dimethylamine;
[2-(1-(4'-Methylbenzenesulfonyl)-5,7-dibromo-2-phenyl-1H-indol-3-yloxy)ethyl]dimethylamine;
[2-(1-(Benzenesulfonyl)-5,7-dibromo-2-methyl-1H-indol-3-yloxy)ethyl]dimethylamine;

[2-(1-(4'-Isopropylbenzenesulfonyl)-5,7-dibromo-2-methyl-1H-indol-3-yloxy)ethyl]dimethylamine;
[2-(1-(2'-Bromo-4'-methoxybenzenesulfonyl)-5,7-dibromo-2-methyl-1H-indol-3-yloxy)ethyl]dimethylamine;
[2-(1-(2',4'-Dimethoxybenzenesulfonyl)-5,7-dibromo-2-methyl-1H-indol-3-yloxy)ethyl]dimethylamine;
[2-(1-(4'-Bromobenzenesulfonyl)-5,7-dibromo-2-methyl-1H-indol-3-yloxy)ethyl]dimethylamine;
[2-(1-(2'-Bromo,4'-Methylbenzenesulfonyl)-5,7-dibromo-2-methyl-1H-indol-3-yloxy)ethyl]dimethylamine;
[2-(1-(2'-Bromobenzenesulfonyl)-5,7-dibromo-2-methyl-1H-indol-3-yloxy)ethyl]dimethylamine;
[2-(1-(4'-Fluorobenzenesulfonyl)-5,7-dibromo-2-methyl-1H-indol-3-yloxy)ethyl]dimethylamine;
[2-(1-(4'-Chlorobenzenesulfonyl)-5,7-dibromo-2-methyl-1H-indol-3-yloxy) ethyl]dimethylamine;
[2-(1-(4'-Methylbenzenesulfonyl)-5,7-dibromo-2-methyl-1H-indol-3-yloxy)ethyl]dimethylamine;
[2-(1-(Benzenesulfonyl)-7-bromo-5-chloro-1H-indol-3-yloxy)ethyl]dimethylamine
[2-(1-(4'-Isopropylbenzenesulfonyl)-7-bromo-5-chloro-1H-indol-3-yloxy)ethyl]dimethylamine;
[2-(1-(2'-Bromo-4'-methoxybenzenesulfonyl)-7-bromo-5-chloro-1H-indol-3-yloxy)ethyl]dimethylamine;
[2-(1-(2',4'-Dimethoxybenzenesulfonyl)-7-bromo-5-chloro-1H-indol-3-yloxy)ethyl]dimethylamine;
[2-(1-(4'-Bromobenzenesulfonyl)-7-bromo-5-chloro-1H-indol-3-yloxy)ethyl]dimethylamine;
[2-(1-(2'-Bromo-4'-Methylbenzenesulfonyl)-7-bromo-5-chloro-1H-indol-3-yloxy)ethyl]dimethylamine;
[2-(1-(2'-Bromobenzenesulfonyl)-7-bromo-5-chloro-1H-indol-3-yloxy)ethyl]dimethylamine;
[2-(1-(4'-Fluorobenzenesulfonyl)-7-bromo-5-chloro-1H-indol-3-yloxy)ethyl]dimethylamine;
[2-(1-(4'-Chlorobenzenesulfonyl)-7-bromo-5-chloro-1H-indol-3-yloxy)ethyl]dimethylamine;
[2-(1-(4'-Methylbenzenesulfonyl)-7-bromo-5-chloro-1H-indol-3-yloxy)ethyl]dimethylamine;
[2-(1-(Benzenesulfonyl)-7-bromo-5-chloro-2-phenyl-1H-indol-3-yloxy)ethyl]dimethylamine;
[2-(1-(4'-Isopropylbenzenesulfonyl)-7-bromo-5-chloro-2-phenyl-1H-indol-3-yloxy)ethyl]dimethylamine;
[2-(1-(2'-Bromo-4'-methoxybenzenesulfonyl)-7-bromo-5-chloro-2-phenyl-1H-indol-3-yloxy)ethyl]dimethylamine;
[2-(1-(2',4'-Dimethoxybenzenesulfonyl)-7-bromo-5-chloro-2-phenyl-1H-indol-3-yloxy)ethyl]dimethylamine;
[2-(1-(4'-Bromobenzenesulfonyl)-7-bromo-5-chloro-2-phenyl-1H-indol-3-yloxy)ethyl]dimethylamine;
[2-(1-(2'-Bromo,4'-Methylbenzenesulfonyl)-7-bromo-5-chloro-2-phenyl-1H-indol-3-yloxy)ethyl]dimethylamine;
[2-(1-(2'-Bromobenzenesulfonyl)-7-bromo-5-chloro-2-phenyl-1H-indol-3-yloxy)ethyl]dimethylamine;
[2-(1-(4'-Fluorobenzenesulfonyl)-7-bromo-5-chloro-2-phenyl-1H-indol-3-yloxy)ethyl]dimethylamine;
[2-(1-(4'-Chlorobenzenesulfonyl)-7-bromo-5-chloro-2-phenyl-1H-indol-3-yloxy)ethyl]dimethylamine;
[2-(1-(4'-Methylbenzenesulfonyl)-7-bromo-5-chloro-2-phenyl-1H-indol-3-yloxy)ethyl]dimethylamine;
[2-(1-(Benzenesulfonyl)-7-bromo-5-chloro-2-methyl-1H-indol-3-yloxy)ethyl]dimethylamine;
[2-(1-(4*-Isopropylbenzenesulfonyl)-7-bromo-5-chloro-2-methyl-1H-indol-3-yloxy)ethyl]dimethylamine;
[2-(1-(2'-Bromo-4'-methoxybenzenesulfonyl)-7-bromo-5-chloro-2-methyl-1H-indol-3-yloxy)ethyl]dimethylamine;
[2-(1-(2',4'-Dimethoxybenzenesulfonyl)-7-bromo-5-chloro-2-methyl-1H-indol-3-yloxy)ethyl]dimethylamine;
[2-(1-(4'-Bromobenzenesulfonyl)-7-bromo-5-chloro-2-methyl-1H-indol-3-yloxy)ethyl]dimethylamine;
[2-(1-(2'-Bromo,4'-Methylbenzenesulfonyl)-7-bromo-5-chloro-2-methyl-1H-indol-3-yloxy)ethyl]dimethylamine;
[2-(1-(2'-Bromobenzenesulfonyl)-7-bromo-5-chloro-2-methyl-1H-indol-3-yloxy)ethyl]dimethylamine;
[2-(1-(4'-Fluorobenzenesulfonyl)-7-bromo-5-chloro-2-methyl-1H-indol-3-yloxy)ethyl]dimethylamine;
[2-(1-(4'-Chlorobenzenesulfonyl)-7-bromo-5-chloro-2-methyl-1H-indol-3-yloxy)ethyl]dimethylamine;
[2-(1-(4'-Methylbenzenesulfonyl)-7-bromo-5-chloro-2-methyl-1H-indol-3-yloxy)ethyl]dimethylamine;
[2-(1-(Benzenesulfonyl)-5-methoxy-1H-indol-3-yloxy)ethyl]dimethylamine;
[2-(1-(4'-Isopropylbenzenesulfonyl)-5-methoxy-1H-indol-3-yloxy)ethyl]dimethylamine;
[2-(1-(2'-Bromo-4'-methoxybenzenesulfonyl)-5-methoxy-1H-indol-3-yloxy)ethyl]dimethylamine;
[2-(1-(2',4'-Dimethoxybenzenesulfonyl)-5-methoxy-1H-indol-3-yloxy)ethyl]dimethylamine;
[2-(1-(4'-Bromobenzenesulfonyl)-5-methoxy-1H-indol-3-yloxy)ethyl]dimethylamine;
[2-(1-(2'-Bromo,4'-Methylbenzenesulfonyl)-5-methoxy-1H-indol-3-yloxy)ethyl]dimethylamine;
[2-(1-(2'-Bromobenzenesulfonyl)-5-methoxy-1H-indol-3-yloxy)ethyl]dimethylamine;
[2-(1-(4'-Fluorobenzenesulfonyl)-5-methoxy-1H-indol-3-yloxy)ethyl]dimethylamine;
[2-(1-(4'-Chlorobenzenesulfonyl)-5-methoxy-1H-indol-3-yloxy)ethyl]dimethylamine;
[2-(1-(4'-Methylbenzenesulfonyl)-5-methoxy-1H-indol-3-yloxy)ethyl]dimethylamine;
[2-(1-(Benzenesulfonyl)-5-methoxy-2-phenyl-1H-indol-3-yloxy)ethyl]dimethylamine;
[2-(1-(4'-Isopropylbenzenesulfonyl)-5-methoxy-2-phenyl-1H-indol-3-yloxy)ethyl]dimethylamine;
[2-(1-(2'-Bromo-4'-methoxybenzenesulfonyl)-5-methoxy-2-phenyl-1H-indol-3-yloxy)ethyl]dimethylamine;
[2-(1-(2',4'-Dimethoxybenzenesulfonyl)-5-methoxy-2-phenyl-1H-indol-3-yloxy)ethyl]dimethylamine;
[2-(1-(4'-Bromobenzenesulfonyl)-5-methoxy-2-phenyl-1H-indol-3-yloxy)ethyl]dimethylamine;
[2-(1-(2'-Bromo,4'-Methylbenzenesulfonyl)-5-methoxy-2-phenyl-1H-indol-3-yloxy)ethyl]dimethylamine;
[2-(1-(2'-Bromobenzenesulfonyl)-5-methoxy-2-phenyl-1H-indol-3-yloxy)ethyl]dimethylamine;
[2-(1-(4'-Fluorobenzenesulfonyl)-5-methoxy-2-phenyl-1H-indol-3-yloxy)ethyl]dimethylamine;
[2-(1-(4'-Chlorobenzenesulfonyl)-5-methoxy-2-phenyl-1H-indol-3-yloxy)ethyl]dimethylamine;
[2-(1-(4'-Methylbenzenesulfonyl)-5-methoxy-2-phenyl-1H-indol-3-yloxy)ethyl]dimethylamine;
[2-(1-(Benzenesulfonyl)-5-methoxy-2-methyl-1H-indol-3-yloxy)ethyl]dimethylamine;
[2-(1-(4'-Isopropylbenzenesulfonyl)-5-methoxy-2-methyl-1H-indol-3-yloxy)ethyl]dimethylamine;
[2-(1-(2'-Bromo-4'-methoxybenzenesulfonyl)-5-methoxy-2-methyl-1H-indol-3-yloxy)ethyl]dimethylamine;
[2-(1-(2',4'-Dimethoxybenzenesulfonyl)-5-methoxy-2-methyl-1H-indol-3-yloxy)ethyl]dimethylamine;
[2-(1-(4'-Bromobenzenesulfonyl)-5-methoxy-2-methyl-1H-indol-3-yloxy)ethyl]dimethylamine;
[2-(1-(2'-Bromo,4'-Methylbenzenesulfonyl)-5-methoxy-2-methyl-1H-indol-3-yloxy)ethyl]dimethylamine;
[2-(1-(2'-Bromobenzenesulfonyl)-5-methoxy-2-methyl-1H-indol-3-yloxy)ethyl]dimethylamine;

[2-(1-(4'-Fluorobenzenesulfonyl)-5-methoxy-2-methyl-1H-indol-3-yloxy)ethyl]dimethylamine;
[2-(1-(4'-Chlorobenzenesulfonyl)-5-methoxy-2-methyl-1H-indol-3-yloxy)ethyl]dimethylamine;
[2-(1-(4'-Methylbenzenesulfonyl)-5-methoxy-2-methyl-1H-indol-3-yloxy)ethyl]dimethylamine;
[2-(1-Benzenesulfonyl-2-phenyl-1H-indol-3-yloxy)ethyl]dimethylamine;
[2-(1-Benzenesulfonyl-5-bromo-2-phenyl-1H-indol-3-yloxy)ethyl]dimethylamine;
[2-(1-Benzenesulfonyl-5-chloro-2-phenyl-1H-indol-3-yloxy)ethyl]dimethylamine;
[2-(1-Benzenesulfonyl-5-fluoro-2-phenyl-1H-indol-3-yloxy)ethyl]dimethylamine;
[2-(1-(2'-Bromobenzenesulfonyl)-2-phenyl-1H-indol-3-yloxy)ethyl]dimethylamine;
[2-(1-(4'-Methylbenzenesulfonyl)-5-fluoro-2-phenyl-1H-indol-3-yloxy)ethyl]dimethylamine;
[2-(1-(4'-Methylbenzenesulfonyl)-5-chloro-2-phenyl-1H-indol-3-yloxy)ethyl]dimethylamine;
[2-(1-Benzenesulfonyl-1H-indol-3-yloxy)ethyl]dimethylamine;
[2-(1-Benzenesulfonyl-5-bromo-1H-indol-3-yloxy)ethyl]dimethylamine;
[2-(1-Benzenesulfonyl-5-nitro-1H-indol-3-yloxy)ethyl]dimethylamine;
[2-(1-(2'-Bromobenzenesulfonyl)-1H-indol-3-yloxy)ethyl]dimethylamine;
[2-(1-(2'-Bromobenzenesulfonyl)-5-bromo-1H-indol-3-yloxy)ethyl]dimethylamine;

or a stereoisomer, or a polymorph, or any suitable combination of above such as a nitrogen oxide thereof; a prodrug of the compound or the nitrogen oxide; a pharmaceutically acceptable salt of the compound, the nitrogen oxide, or the prodrug; or a solvate or hydrate of the compound, the nitrogen oxide, the prodrug or the pharmaceutically acceptable salt.

The present invention also relates to the process for preparing the compound of the general formula (I) its stereoisomers, its radioisotopes, its geometric forms, its N-oxide, its polymorphs, its pharmaceutically acceptable salts, its pharmaceutically acceptable solvates, its useful bioactive metabolites and any suitable combination of above.

In the case of the compounds of general formula (I), where tautomerism may exist, the present invention relates to all of the possible tautomeric forms and the possible mixture thereof.

The present invention also relates to the stereoisomers, which as a rule are obtained as racemates that can be separated into the optically active isomers in a manner known per se.

The present invention also relates to radio-labeled isotopes, which are identical to those defined in the general formula (I), but for the fact that one or more atoms are replaced by an atom having an atomic mass or mass number different from the atomic mass or mass number found usually in nature. Examples of isotopes that can be incorporated into compounds of the invention include isotopes of hydrogen, carbon, nitrogen, oxygen, phosphorus, fluorine, chlorine, iodine, bromine and mTecnitium, exemplified by $^{2}H$, $^{3}H$, $^{11}C$, $^{13}C$, $^{14}C$, $^{13}N$, $^{15}N$, $^{15}O$, $^{18}F$, $^{99m}Tc$, $^{31}P$, $S$, $^{123}I$ and $^{125}I$. Those compounds of general formula (I) as described earlier containing the aforementioned isotopes and/or other isotopes of other atoms are within the scope of this invention.

In the case of the compounds of general formula (I) containing geometric isomerism the present invention relates to all of these geometric isomers.

The term "nitrogen oxide" or "N-oxide" refers to the oxidation of at least one of the two nitrogens in the compounds of general formula (I) (e.g., mono- or di-oxide). The nitrogen mono-oxides may exist as a single positional isomer or a mixture of 2° positional isomers (e.g., a mixture of 1-N-oxide and 4-N-oxide piperazine or a mixture of 1-N-oxide and 4-N-oxide piperazines).

Suitable pharmaceutically acceptable acid addition salts of compounds of the general formula (I) can be prepared of the aforementioned base compounds of this invention are those which form non-toxic acid addition salts, includes, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate, palmoate and oxalate. Pharmaceutically acceptable salts forming part of this invention are intended to define but not limited to the above list.

Suitable pharmaceutically acceptable base addition salts of compounds of the general formula (I) can be prepared of the aforementioned acid compounds of this invention are those which form non-toxic base addition salts, includes, salts containing pharmaceutically acceptable cations, such as Lithium, sodium, potassium, calcium and magnesium, salts of organic bases such as, lysine, arginine, guanidine, diethanolamine, choline, tromethamine and the like; ammonium or substituted ammonium salts.

Pharmaceutically acceptable salts forming part of this invention are intended to define but not limited to the above list.

In addition, pharmaceutically acceptable salts of the compound of formula (I) can be obtained by converting derivatives which have tertiary amino groups into the corresponding quarternary ammonium salts in the methods known in the literature by using quarternizing agents. Possible quarternizing agents are, for example, alkyl halides such as methyl iodide, ethyl bromide and n-propyl chloride, including arylalkyl halides such as benzyl chloride or 2-phenylethyl bromide.

In the addition to pharmaceutically acceptable salts, other salts are included in the invention. They may serve as intermediates in the purification of the compounds, in the preparation of other salts, or in the identification and characterization of the compounds or intermediates.

The pharmaceutically acceptable salts of compounds of formula (I) may exists as solvates, such as with water, methanol, ethanol, dimethylformamide, ethyl acetate, and the like. Mixtures of such solvates can also be prepared. The source of such solvate can be from the solvent of crystallization, inherent in the solvent preparation or crystallization, or adventitious to such solvent. Such solvates are within the scope of this invention.

The invention also encompasses the pharmaceutically acceptable prodrugs of the compounds of the formula (I). A prodrug is a drug which has been chemically modified and may be biologically in-active at the site of action, but which may be degraded or modified by one or more enzymatic or other in-vivo processes to the parent form. This prodrug should have a different pharmacokinetic profile than the parent, enabling easier absorption across the mucosal epithelium, better salt formation, or solubility, and/or improved systemic stability (an increase in the plasma half-life, for example). Typically, such chemical modifications include the following:

1. ester or amide derivatives which may be cleaved by esterases or lipases;
2. peptides which may be recognized by specific or non-specific proteases; or
3. derivatives that accumulate at a site of action through membrane selection of a prodrug from or a modified prodrug form; or
4. any combination of 1 to 3, above.

Conventional procedures for the selection and preparation of suitable prodrug derivatives are described, for example, in H. Bundgard, Design of prodrugs, (1985).

Another aspect of the present invention comprises of a pharmaceutical composition, containing at least one of the compounds of the general formula (I), their derivatives, their analogs, their derivatives, their stereoisomers, their polymorphs, their pharmaceutically acceptable salts, their pharmaceutically acceptable solvates thereof as an active ingredient, together with pharmaceutically employed carriers, auxiliaries and the like.

An effective amount of a compound of general formula (I) or its salt is used for producing medicaments of the present invention, along with conventional pharmaceutical auxiliaries, carriers and additives.

The present invention also relates to the pharmaceutically acceptable compositions containing them, and the use of these compounds and compositions in medicine.

The compounds of general formula (I) of this invention are useful in the treatment and/or prophylaxis of a condition wherein modulation of 5-HT activity is desired.

The compounds of general formula (I) of this invention are useful in the treatment and/or prophylaxis of a condition wherein modulation of melatonin activity is desired.

The compounds of general formula (I) of this invention are useful in the treatment and/or prophylaxis of a condition wherein modulation of 5-HT and melatonin activities gives desired effect.

The present invention provides for use of the compounds of general formula (I) according to above, for the manufacture of the medicaments for the potential use in the treatment and/or prophylaxis of certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Disorder/Hyperactivity Syndrome), personality disorders, psychosis, paraphrenia, psychotic depression, mania, schizophrenia, schizophreniform disorders, withdrawal from drug abuse such as cocaine, ethanol, nicotine and benzodiazepines, panic attacks, chronobiological abnormalities, circadian rhythms, anxiolytic, osteoporosis, ischemic stroke, lower the risk of SIDS in young infants with low endogenous melatonin levels, reproduction, glaucoma, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The compounds of the invention are also expected to be of use in the treatment of certain GI (Gastrointestinal) disorders such as IBS (Irritable bowel syndrome) or chemotherapy induced emesis.

The compounds of the invention are also expected to be of use in the modulation of eating behavior and these compounds can also be used to reduce morbidity and mortality associated with the excess weight.

The present invention provides a method for the treatment of a human or a animal subject suffering from certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Hyperactivity Disorder), personality disorders, psychosis, paraphrenia, psychotic depression, mania, schizophrenia, schizophreniform disorders, withdrawal from drug abuse such as cocaine, ethanol, nicotine and benzodiazepines, panic attacks, chronobiological abnormalities, circadian rhythms, anxiolytic, osteoporosis, ischemic stroke, lower the risk of SIDS in young infants with low endogenous melatonin levels, reproduction, glaucoma, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The present invention also provides a method for modulating 5-HT and/or melatonin receptor function desired in certain cases.

Compounds of the present invention may be administered in combination with other pharmaceutical agents, such as apo-B/MTP inhibitors, MCR-4 agonists, CCK-A agonists, monoamine reuptake inhibitors, sympathomimetic agents, adrenergic receptor agonists, dopamine agonists, melanocyte-stimulating hormone receptor analogs, cannabinoid 1 receptor antagonists, melanin concentrating hormone antagonists, leptins, leptin analogs, leptin receptor agonists, galanin antagonists, lipase inhibitors, bombesin agonists, neuropeptide-Y antagonists, thyromimetic agents, dehydroepiandrosterone or analogs thereof, glucocorticoid receptor agonists or antagonists, orexin receptor antagonists, urocortin binding protein antagonists, glucagon-like peptide-1 receptor agonists, ciliary neurotrophic factors, AGRPs (human agouti-related proteins), ghrelin receptor antagonists, histamine 3 receptor antagonists or reverse agonists, neuromedin U receptor agonists, and the like, in a therapeutically effective amount via a suitable pharmaceutical composition, to achieve the desired effect in mammals as well as humans.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace all the meanings such as preventative, prophylactic and palliative.

The term "compounds of the present invention" (unless specifically identified otherwise) refer to compounds of Formulae (I), nitrogen oxides thereof, prodrugs of the compounds or nitrogen oxides, pharmaceutically acceptable salts of the compounds, nitrogen oxides, and/or prodrugs, and hydrates or solvates of the compounds, nitrogen oxides, salts, is and/or prodrugs, as well as, all stereoisomers (including diastereoisomers and enantiomers), tautomers and isotopically labeled compounds.

The present invention also relates to the novel intermediates, represented by genera) formulae (II), (VI), (VII) and (IX) their stereoisomers, their radioisotopes, their geometric forms, their N-oxide, their salts, their solvates and any suitable combination of above, involved in preparing the compounds of general formula (I) and the process of preparation of such intermediates.

DETAILED DESCRIPTION OF THE INVENTION

The present invention relates to compounds of general formula (I), their stereoisomers, their radioisotopes, their geometric forms, their N-oxides, their polymorphs, their pharmaceutically acceptable salts, their pharmaceutically acceptable solvates, their useful bioactive metabolites and any suitable combination of above.

The present invention relates to compounds of general formula (I), described as follows,

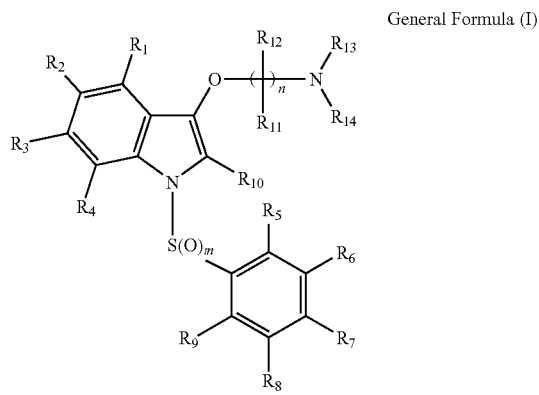

General Formula (I)

wherein $R_1$, $R_2$, $R_3$, $R_4$, $R_5$, $R_6$, $R_7$, $R_8$, $R_9$, $R_{11}$ and $R_{12}$ may be same or different, and represent hydrogen, halogen, perhaloalkyl, hydroxy, thio, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, (CV $C_7$)cycloalkenyl, bicycloalkyl, bicycloalkenyl, ($C_1$-$C_{12}$)alkoxy, cyclo($C_3$-$C_7$) alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxyamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_8$ together with carbon atoms to which they are attached may form a five or a six membered ring, optionally containing one or more double bonds and optionally containing one or more heteroatoms selected from O, N, S and combinations of double bond and heteroatoms; or $R_{11}$ and $R_{12}$ together with carbon atoms to which they are attached may form a three to a six membered ring, optionally containing one or more double bonds and optionally containing one or more heteroatoms selected from O, N, S and combinations of double bond and heteroatoms.

$R_{10}$ represents hydrogen, halogen, perhaloalkyl, substituted or unsubstituted groups selected from linear or branched ($C_1$-$C_3$)alkyl and aryl.

$R_{13}$ and $R_{14}$ represents hydrogen, alkyl, aryl, aralkyl or together with nitrogen atom form a cyclic three to seven membered ring, optionally, $R_{11}$ and $R_{13}$ together may form a part of cyclic structure along with the intervening nitrogen and carbon atoms; the heterocycle may have either one, two or three double bonds; optionally it may also contain one to three heteroatom selected from the group of oxygen, nitrogen and sulfur, and includes ring-fused with any carbocyclic or heterocyclic ring, which can be saturated or unsaturated.

"n" is an integer ranging from 1 to 8, preferably 1 to 4, wherein the carbon chains which "n" represents may be either linear or branched.

"m" is an integer ranging from 0 to 2 preferably m is 1 or 2; along with the proviso that whenever m=2 and each of $R_5$, $R_6$, $R_7$, $R_8$ and $R_9$ are hydrogens then all of $R_1$, $R_2$, $R_3$, $R_4$ and $R_{10}$) together are never hydrogens.

Suitable groups represented by $R_1$, $R_2$, $R_3$, $R_4$, $R_5$, $R_6$, $R_7$, $R_8$, $R_9$, $R_{10}$, $R_{11}$ and $R_{12}$ wherever applicable may be selected from halogen atom such as fluorine, chlorine, bromine or iodine; perhaloalkyl particularly perhalo($C_1$-$C_6$)alkyl such as fluoromethyl, difluoromethyl, trifluoromethyl, trifluoroethyl, fluoroethyl, difluoroethyl and the like; substituted or unsubstituted ($C_1$-$C_{12}$)alkyl group, especially, linear or branched ($C_1$-$C_8$)alkyl group, such as methyl, ethyl, n-propyl, iso-propyl, n-butyl, iso-butyl, t-butyl, n-pentyl, iso-pentyl, hexyl, iso-hexyl, heptyl, octyl and the like; cyclo($C_3$-$C_7$)alkyl group such as cyclopropyl, cyclobutyl, cyclopentyl, cyclohexyl, cycloheptyl, the cycloalkyl group may be substituted; cyclo($C_3$-$C_7$)alkenyl group such as cyclopentenyl, cyclohexenyl, cycloheptynyl, cycloheptadienyl, cycloheptatrienyl and the like, the cycloalkenyl group may be substituted; ($C_1$-$C_{12}$) alkoxy, especially, ($C_1$-$C_6$)alkoxy group such as methoxy, ethoxy, propyloxy, butyloxy, iso-propyloxy and the like, which may be substituted; cyclo($C_3$-$C_7$) alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aralkyl group such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, imidazolyl, oxadiazolyl, tetrazolyl, benzopyranyl, benzofuranyl and the like, the heteroaryl group may be substituted; heterocyclo($C_1$-$C_6$) alkyl, such as pyrrolidinealkyl, piperidinealkyl, morpholinealkyl, thiomorpholinealkyl, oxazolinealkyl and the like, the heterocyclo($C_1$-$C_6$)alkyl group may be substituted; heteroaralkyl group such as furanylmethyl, pyridinylmethyl, oxazolylmethyl, oxazolylethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be substituted; acyl groups such as acetyl, propionyl or benzoyl, the acyl group may be substituted; acyloxy group such as $CH_3COO$, $CH_3CH_2COO$, $C_6H_5COO$ and the like which may optionally be substituted, acylamino group such as $CH_3CONH$, $CH_3CH_2CONH$, $C_3H_7CONH$, $C_6H_5CONH$ which may be substituted, ($C_1$-$C_6$)monoalkylamino group such as $CH_3NH$, $C_2H_5NH$, $C_3H_7NH$, $C_6H_{13}NH$ and the like, which may be substituted, $(C_1-C_6)$dialkylamino group such as $N(CH_3)_2$, $CH_3(C_2H_5)N$ and the like, which may be substituted; arylamino group such as $C_6H_5NH$, $CH_3(C_6H_5)N$, $C_6H_4(CH_3)NH$, $NH-C_6H_4$-Hal and the like, which may be substituted; arylalkylamino group such as $C_6H_5CH_2NH$, $C_6H_5CH_2CH_2NH$, $C_6H_5CH_2NCH_3$ and the like, which may be substituted; hydroxy$(C_1-C_6)$alkyl which may be substituted, amino$(C_1-C_6)$alkyl which may be substituted; mono $(C_1-C_6)$alkylamino$(C_1-C_6)$alkyl, di$(C_1-C_6)$alkylamino$(C_1-C_6)$alkyl group which may be substituted, alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; $(C_1-C_6)$alkylthio, thio$(C_1-C_6)$alkyl which may be substituted, alkoxycarbonylamino group such as $C_2H_5OCONH$, $CH_3OCONH$ and the like which may be substituted; aryloxycarbonylamino group as $C_2H_5OCONH$, $C_6H_5OCONCH_3$, $C_6H_5OCONC_2H_5$, $C_6H_5CH_5OCONH$, $C_6H_4(OCH_3)OCONH$ and the like which may be substituted; aralkoxycarbonylamino group such $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4CH_3CH_2OCONH$, $C_6H_4OCH_3CH_2OCONH$ and the like, which may be substituted; aminocarbonylamino group; $(C_1-C_6)$alkylaminocarbonylamino group, di$(C_1-C_6)$alkylaminocarbonylamino group; $(C_1-C_6)$alkylamidino group, $(C_1-C_6)$alkylguanidino, di$(C_1-C_6)$alkylguanidino groups, hydrazino and hydroxylamino groups; carboxylic acid or its derivatives such as amides, like $CONH_2$, alkylaminocarbonyl like $CH_3NHCO$, $(CH_3)_2NCO$, $C_2H_5NHCO$, $(C_2H_5)_2NCO$, arylaminocarbonyl like $PhNHCO$, $NapthylNHCO$ and the like, aralkylaminocarbonyl such as $PhCH_2NHCO$, $PhCH_2CH_2NHCO$ and the like, heteroarylaminocarbonyl and heteroaralkylamino carbonyl groups where the heteroaryl groups are as defined earlier, heterocyclylaminocarbonyl where the heterocyclyl group is as defined earlier, carboxylic acid derivatives such as esters, wherein the ester moieties are alkoxycarbonyl groups such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, heteroaryloxycarbonyl, heteroaralkoxycarbonyl, wherein the heteroaryl group is as defined earlier, heterocycloxycarbonyl where heterocycle is as defined earlier and these carboxylic acid derivatives may be substituted; sulfonic acid or its derivatives such as $SO_2NH_2$, $SO_2NHCH_3$, $SO_2N(CH_3)_2$, $SO_2NHCF_3$, $SO_2NHCO(C_1-C_6)$alkyl, $SO_2NHCOaryl$ where the aryl group is as defined earlier and the sulfonic acid derivatives may be substituted; phosphoric acid and its derivatives as $P(O)(OH)_2$, $P(O)OC_1-C_6$-alkyl$)_2$, $P(O)(O\text{-aryl})_2$ and the like.

Suitable cyclic structures formed by the two adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ or $R_{11}$ and $R_{12}$ together with the carbon atoms to which they are attached contain 5 to 6 ring atoms which may optionally contain one or more heteroatoms selected from oxygen, nitrogen or sulfur and optionally contain one or more double bonds and optionally contain combination of double bond and hetero atoms as described earlier. The cyclic structures may be optionally substituted phenyl, naphthyl, pyridyl, furanyl, thienyl, pyrrolyl, imidazolyl, pyrimidinyl, pyrazinyl and the like. Suitable substituents on the cyclic structure formed by $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ or $R_{11}$ and $R_{12}$ together with the adjacent carbon atoms to which they are attached include oxo, hydroxy, halogen atom such as chlorine, bromine and iodine; nitro, cyano, amino, formyl, $(C_1-C_3)$alkyl, $(C_1-C_3)$alkoxy, thioalkyl, alkylthio phenyl or benzyl groups.

$R_{13}$ and $R_{14}$ preferably represents hydrogen, substituted or unsubstituted linear or branched $(C_1-C_{12})$alkyl like methyl, ethyl, n-propyl, iso-propyl, n-butyl, iso-butyl, pentyl, hexyl, octyl and the like; aryl group such as phenyl or naphthyl, the aryl group may be substituted; cyclo$(C_3-C_7)$alkyl group such as cyclopropyl, cyclobutyl, cyclopentyl, cyclohexyl, cycloheptyl, the cycloalkyl group may be substituted; the aralkyl group may be substituted and the substituted aralkyl is a group such as $CH_3C_6H_4CH_2$, $Hal-C_6H_4CH_2$, $CH_3OC_6H_4CH_2(CH_3OC_6H_4CH_2CH_2$ and the like; $(C_3-C_7)$ cycloheteroalkyl with heteroatoms like "Oxygen", "Nitrogen" and "Sulfur" and optionally containing one or two double or triple bonds.

Suitable hetero cyclic rings formed by either $R_{11}$ and $R_{13}$ be selected from pyrrolyl, imidazolyl, pyrimidinyl, pyrazinyl, pyrrolidinyl, piperidinyl, morpholinyl, piperazinyl, oxazolinyl, diazolinyl and the like, the heterocyclyl group may be substituted; heteroaryl group such as pyridyl, pyrrolyl, oxazolyl, imidazolyl, oxadiazolyl, tetrazolyl, benzopyranyl and the like, the heteroaryl group may be substituted; heterocyclo$(C_1-C_6)$alkyl, such as pyrrolidinealkyl, piperidinealkyl, morpholinealkyl, thiomorpholinealkyl, oxazolinealkyl and the like, the heterocyclo$(C_1-C_6)$alkyl group may be substituted; heteroaralkyl group such as furanmethyl, pyridinemethyl, oxazolemethyl, oxazolethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be further substituted.

Compounds of the present invention may be synthesized by synthetic routes that include processes analogous to those known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

For example, a sulfide linkage (i.e., m=0) can be easily oxidized to its corresponding sulfinyl or sulfonyl group (i.e., m=1 or m=2) using common oxidation procedures (e.g., oxidation with m-chloroperbenzoic acid). Suitable values for Lg are for example, a halogeno, for example a chloro, bromo, iodo, or aryl or alkyl sulfonyloxy group, for example, a methanesulfonyloxy or toluene-4-sulfonyloxy group or trifluoroacetate.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include trifluoroacetyl, t-butoxycarbonyl (BOC), benzyloxycarbonyl (CBz) and Fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991. The protecting groups may be removed at a convenient subsequent stage using methods known from the art.

The present invention also provides processes for preparing compounds of general formula (I) as defined above their stereoisomers, their polymorphs, their pharmaceutically acceptable salts, their pharmaceutically acceptable solvates and novel intermediates involved therein, which are as described below. There are few methods already reported in the literature including GB patent specification 1 306 230, U.S. Pat. No. 3,509,163. These methods and references therein are included herein by reference.

In the description and the reaction scheme which follow $R_1, R_2, R_3, R_4, R_5, R_6, R_7, R_8, R_9, R_{10}, R_{11}, R_{12}, R_{13}, R_{14}$, m and n are as defined previously, while Lg, R, $R_a$, $R_b$ and $R_c$ is as defined elsewhere in the specification.

Scheme 1:

Compounds of general formula (I) may be prepared by reacting a compound of formula (II) given below,

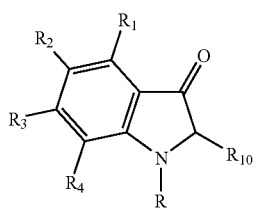

(II)

wherein $R_1, R_2, R_3, R_4,$ and $R_{10}$ are as defined in relation to formula (I), further $R_{10}$ could be protected form thereof; R represents either of a suitable N-protecting group, or a group such as,

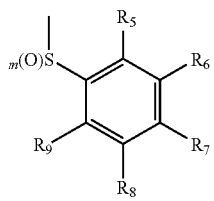

wherein m, $R_5, R_6, R_7, R_8$ and $R_9$ are as defined earlier, with a compound of formula (III) or its acid addition salt,

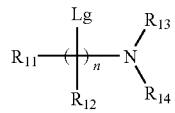

(III)

wherein n, $R_{11}, R_{12}, R_{13}$, and $R_{14}$ are as defined in relation to compound of formula (I) or precursor thereof and Lg is a leaving group; and thereafter if necessary;

i) converting a compound of the formula (I) into another compound of the formula (I)

ii) removing any protecting groups; or iii) forming a pharmaceutically acceptable salt, solvate or prodrug thereof.

In case when R is a suitable protecting group, an additional step as described in Scheme 2 is required to prepare compounds of formula (I).

The above reaction is preferably carried out in a solvent such as THF, toluene, acetone, ethyl acetate, DMF, DMSO, DME, N-methylpyrrolidone, methanol, ethanol propanol and the like and preferably using either acetone or DMF. The inert atmosphere may be maintained by using inert gases such as $N_2$, Ar or He. The reaction may be affected in the presence of a base such as $K_2CO_3$, NaOH, $Na_2CO_3$, NaH and the like as well as the mixtures thereof. The reaction mixture is generally heated to an elevated temperature or reflux temperature of the solvent, until the reaction is complete. A wide variety of basic agents can be used in this condensation. However, preferred basic agents are amines, such as trimethylamine, triethylamine, tributylamine, N-methylmorpholine, piperidine, N-methylpiperidine, pyridine and 4-(N,N-dimethylamino) pyridine, with a preferred basic agent being $K_2CO_3$. Reaction times of about 30 minutes to 72 hours are common. At the end of reaction, the volatile components are removed under reduced pressure. The reaction mixture can be optionally acidified before workup. The product can be isolated by precipitation, washed, dried and further purified by standard methods such as recrystallization, column chromatography etc.

Optional step (i) and (ii) can be carried out using conventional methods. These will depend upon the precise nature of the substituents $R_1, R_2, R_3, R_4, R_{10}, R_{11}, R_{12}, R_{13}$, and $R_{14}$ in each case. Examples of suitable reactions are illustrated hereinafter.

Scheme 2:

Alternatively, compounds of formula (I) may be prepared by reacting a compound of formula (IV) given below,

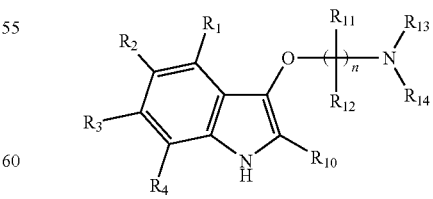

(IV)

wherein n, $R_1, R_2, R_3, R_4, R_{11}, R_{12}, R_{13}$, and $R_{14}$ are as defined in relation to formula (I), $R_{10}$ is as defined elsewhere in the definition of compounds of formula (IV), with a compound of formula (V)

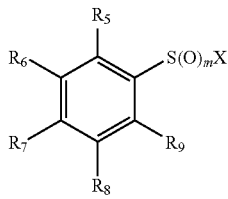

(V)

wherein m, $R_5$, $R_6$, $R_7$, $R_8$ and $R_9$, are as defined in relation to formula (I) and X is a halogen, preferably chloro or bromo; and thereafter if desired or necessary carrying out additional steps described above.

Compounds of formula (IV) and (V) are suitably reacted together in an inert organic solvent which includes, aromatic hydrocarbons such as toluene, o-, m-, p-xylene; halogenated hydrocarbons such as methylene chloride, chloroform, and chlorobenzene; ethers such as diethylether, diisopropyl ether, tert-butyl methyl ether, dioxane, anisole, and tetrahydrofuran; nitriles such as acetonitrile and propionitrile; ketones such as acetone, methyl ethyl ketone, diethyl ketone and tert-butyl methyl ketone; alcohols such as methanol, ethanol, n-propranol, n-butanol, tert-butanol and also DMF (N,N-dimethylformamide), DMSO(N,N-dimethyl sulfoxide) and water. The preferred list of solvents includes DMSO, DMF, acetonitrile and THF. Mixtures of these in varying ratios can also be used. Suitable bases are, generally, inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, lithium oxide, sodium oxide, magnesium oxide and calcium oxide; alkali metal hydrides and alkaline earth metal hydrides such as lithium hydride, sodium hydride, potassium hydride and calcium hydride; alkali metal amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogen carbonates and alkaline earth metal hydrogen carbonates such as sodium hydrogen carbonate; organometallic compounds, particularly alkali-metal alkyls such as methyl lithium, butyl lithium, phenyl lithium; alkyl magnesium halides such as methyl magnesium chloride, and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, and N-methylpiperidine, pyridine. Sodium hydroxide, Sodium methoxide, Sodium ethoxide, potassium hydroxide potassium carbonate and triethylamine are especially preferred. Suitably the reaction may be effected in the presence of phase transfer catalyst such as tetra-n-butylammonium hydrogensulphate and the like. The inert atmosphere may be maintained by using inert gases such as $N_2$, Ar or He. Reaction times may vary from 1 to 24 hrs, preferably from 2 to 6 hours, whereafter, if desired, the resulting compound is continued into a salt thereof.

Compounds of formula (IV) may be prepared as reported in the literature or by the method analogous to that described in Scheme 1, between the compound of formula (II) and (III), wherein ring nitrogen is protected before the reaction.

Scheme 3:

Alternatively, compounds of formula (I) may be prepared by reacting a compound of formula (VI)

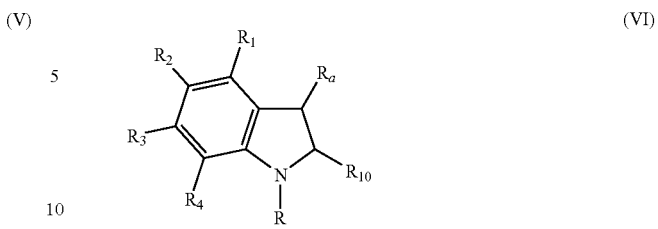

(VI)

wherein $R_1$, $R_2$, $R_3$, $R_4$ and $R_{10}$ are as defined in relation to formula (I), $R_{10}$ could also be protected form thereof; $R_a$ is defined as either hydrogen, halogen (such as chloro or bromo), lithio, trimethylsilyl, lower alkoxy, boronic acid or trifluoromethanesulfonate groups; R is defined as a suitable N-protecting group or a group such as,

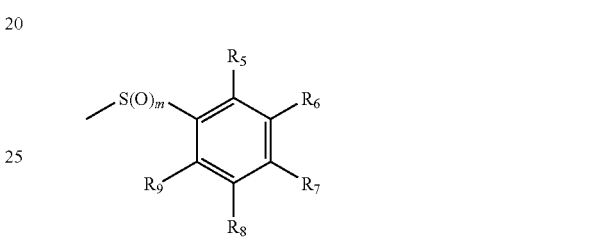

wherein m, $R_5$, $R_5$, $R_7$, $R_8$ and $R_9$ are as defined earlier for compound of formula (I), and with a compound of formula (III) or its acid addition salt

(III)

wherein n, $R_{11}$, $R_{12}$, $R_{13}$, and $R_{14}$ are as defined in relation to compound of formula (I) or precursor thereof and Lg is a leaving group; or its acid addition salt of compound of formula (III) may be used; and thereafter if desired or necessary carrying out additional steps described above.

Suitable substituents for Lg is either a hydroxy, sulfonyloxy group or a halogeno as defined earlier and the selection is based upon the nature of substitution at $R_a$. Whenever R is acetyl, an additional step described in Scheme 2 is required to prepare compounds of general formula (I).

The above reaction is preferably carried out in a solvent such as THF, toluene, ethyl acetate, acetone, water, DMF, DMSO, DME, and the like or a mixture thereof, and preferably using either acetone or DMF. The inert atmosphere may be maintained by using inert gases such as $N_2$, Ar or He. The reaction may be affected in the presence of a base such as $K_2CO_3$, $Na_2CO_3$, NaH or mixtures thereof. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

Scheme 4:

Alternatively, compounds of formula (I) may be prepared by reacting a compound of formula (VII)

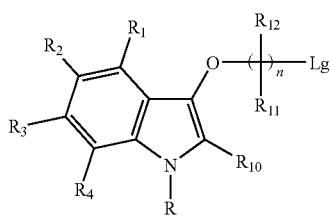

wherein $R_1$, $R_2$, $R_3$, $R_4$, $R_{10}$, $R_{11}$ and $R_{12}$ are as defined in relation to formula (I), $R_{10}$ is a group $R_{10}$ as defined in relation to formula (I) or protected form thereof; R is defined as a suitable N-protecting group, or a group such as,

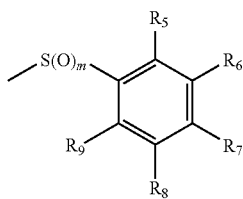

wherein m, $R_5$, $R_6$, $R_7$, $R_8$ and $R_9$ are as defined earlier for compound of formula (I), with a compound of formula (VIII)

 (VIII)

wherein $R_{13}$ and $R_{14}$ are as defined in relation to compound of formula (I) or precursor thereof or with its acid addition salt thereof; and thereafter if desired or necessary carrying out additional steps described above.

Suitable values for Lg are for example, a halogeno or sulfonyloxy group, for example a chloro, bromo, iodo, methanesulfonyloxy or toluene-4-sulfonyloxy group or trifluoroacetyl.

Scheme 5:

Alternatively, compounds of formula (I) may be prepared by reductive alkylation of compounds of formula (IX)

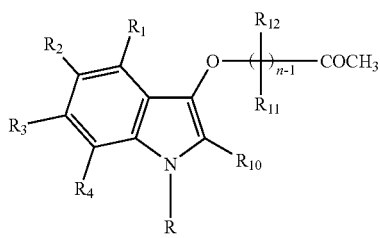

wherein n, $R_1$, $R_2$, $R_3$, $R_4$, $R_{10}$, $R_{11}$ and $R_{12}$ are as defined in relation to formula (I), $R_{10}$ could also be a protected form thereof; R is defined as a suitable N-protecting group or a group such as,

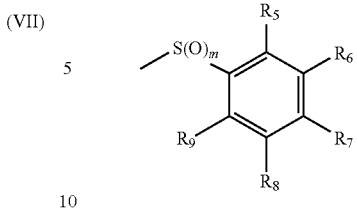

wherein m, $R_5$, $R_6$, $R_7$, $R_8$ and $R_9$ are as defined earlier for compound of formula (I), with a compound of formula (VIII)

 (VIII)

wherein $R_{13}$ and $R_{14}$ are as defined in relation to compound of formula (I) or precursor thereof or with its acid addition salt thereof; and thereafter if desired or necessary carrying out additional steps described above.

Scheme 6:

Alternatively, compounds of formula (I) in which $R_{13}$ is lower alkyl radical such as $C_{1-6}$alkyl, a cycloalkyl containing 3-8 carbon atoms or a benzyl radical in which phenyl ring is substituted and $R_{14}$ is hydrogen may be prepared from another compound of formula (X)

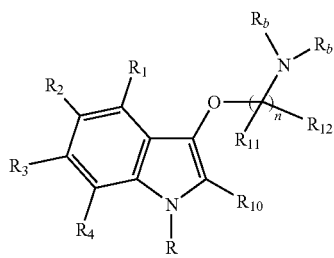

Where n, $R_1$, $R_2$, $R_3$, $R_4$, $R_{10}$, $R_{11}$ and $R_{12}$ are as defined in relation to formula (I), $R_{10}$ is a group $R_{10}$ as defined in relation to formula (I) or protected form thereof; and in which $R_b$ represents hydrogen atom or a benzyl group in which phenyl ring is substituted and removable by hydrogenolysis, R is defined as a suitable N-protecting group or a group such as,

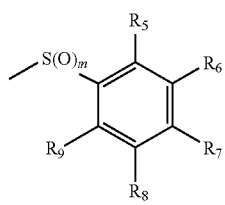

wherein m, $R_5$, $R_6$, $R_7$, $R_8$ and $R_9$ are as defined earlier for compound of formula (I), with a compound of formula (XI)

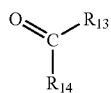 (XI)

wherein $R_{13}$ and $R_{14}$ are as defined in relation to compound of formula (I) or precursor thereof or with its acid addition salt thereof; and thereafter if desired or necessary carrying out additional steps described above.

Similarly, when $R_{10}$, $R_{13}$ and $R_{14}$ represents hydrogen atoms, these compounds may be prepared according to this invention by hydrogenolysing the corresponding indole derivative, in which above substituents represent one or more benzyl groups removable by hydrogenolysis.

Furthermore, indole derivatives of the general formula (I) in which $R_{13}$ is benzyl or a substituted benzyl group removable by hydrogenolysis and $R_{14}$ is hydrogen, may according to this invention be prepared by partially hydrogenolysing the corresponding indole derivative in which $R_{14}$ is identical to the substitutent $R_{13}$ above. The said hydrogenolysis is performed in a solvent such as ethanol in the presence of a suitable catalyst, e.g. palladium on carbon. The reaction is performed in a solvent such as methanol or ethanol in the presence of hydrogen and a suitable catalyst such as palladium on carbon.

Novel intermediates of general formula (II) are represented as given below,

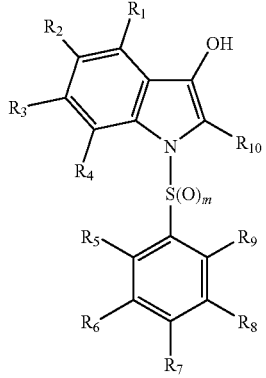

(II)

wherein $R_1$, $R_2$, $R_3$, $R_4$, $R_5$, $R_6$, $R_7$, $R_8$ and $R_9$ may be same or different, and represent hydrogen, halogen, perhaloalkyl, hydroxy, thio, amino, nitro, cyano, formyl, amidino, guanidino, substituted or unsubstituted groups selected from linear or branched $(C_1-C_{12})$alkyl, $(C_2-C_{12})$alkenyl, $(C_2-C_{12})$alkynyl, $(C_3-C_7)$cycloalkyl, $(C_3-C_7)$cycloalkenyl, bicycloalkyl, bicycloalkenyl, $(C_1-C_{12})$alkoxy, cyclo$(C_3-C_7)$alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from O, N, S and combinations of double bond and heteroatoms; "m" is an integer ranging from 0 to 2 preferably m is 1 or 2; $R_{10}$ represents hydrogen, halogen, perhaloalkyl, substituted or unsubstituted groups selected from linear or branched $(C_1-C_3)$alkyl and aryl; and its stereoisomers and its salts Numerous processes to prepare the compounds of formula (II) can be found in literature. Some of them are J. Heterocyclic Chemistry, 16, 221 (1979), JP patent publication 57200362 A, U.S. Pat. No. 3,860,608 and DE 111890. Alternatively, compounds of formula (II) may suitably be prepared by conventional methods for oxidization of indole-3-carboxaldehydes as described in literature (Chem. Pharm. Bull, 1985, 33, 1843, wherein HMPA, mCPBA are used as oxidizing agent).

Novel intermediates of general formula (VI) are represented as given below.

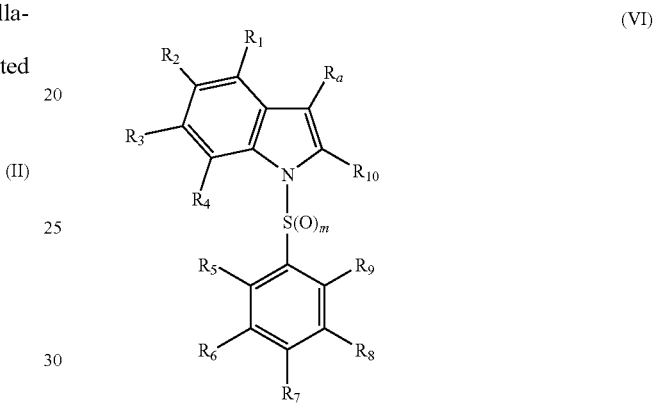

(VI)

wherein $R_1$, $R_2$, $R_3$, $R_4$, $R_5$, $R_6$, $R_7$, $R_8$ and $R_9$ may be same or different, and represent hydrogen, halogen, perhaloalkyl, hydroxy, thio, amino, nitro, cyano, formyl, amidino, guanidino, substituted or unsubstituted groups selected from linear or branched $(C_1-C_{12})$alkyl, $(C_2-C_{12})$alkenyl, $(C_2-C_{12})$alkynyl, $(C_3-C_7)$cycloalkyl, $(C_3-C_7)$cycloalkenyl, bicycloalkyl, bicycloalkenyl, $(C_1-C_{12})$alkoxy, cyclo$(C_3-C_7)$alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from O, N, S and combinations of double bond and heteroatoms; and "m" is an integer ranging from 0 to 2 preferably m is 1 or 2; $R_{10}$ represents hydrogen, halogen, perhaloalkyl, substituted or unsubstituted groups selected from linear or branched $(C_1-C_3)$alkyl and aryl;

$R_a$ is defined as either hydrogen, halogen (such as chloro or bromo), lithio, trimethylsilyl, lower alkoxy, boronic acid or trifluoromethanesulfonate groups; and its stereoisomers and its salts; along with the proviso that whenever R is SO$_2$Ph, and all of R$_1$, R$_2$, R$_3$, R$_4$, R$_5$, R$_6$, R$_7$, R$_8$, R$_9$ and R$_{10}$ substituents are hydrogen's R$_a$ never either of bromo, lithio, trimethylsilyl, boronic acid or trifluoromethanesulfonate groups.

Procedure to prepare compounds of formula (VI) is as reported in Heterocycles, vol. 30, no. 1, 1990.

Novel intermediates of general formula (VII) are represented as given below,

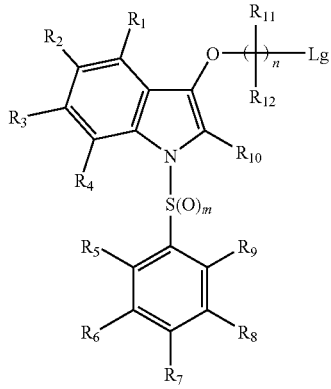

(VII)

wherein R$_1$, R$_2$, R$_3$, R$_4$, R$_5$, R$_6$, R$_7$, R$_8$, R$_9$, R$_{11}$ and R$_{12}$ may be same or different, and represent hydrogen, halogen, perhaloalkyl, hydroxy, thio, amino, nitro, cyano, formyl, amidino, guanidino, substituted or unsubstituted groups selected from linear or branched (C$_1$-C$_{12}$)alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, (C$_1$-C$_{12}$)alkoxy, cyclo(C$_3$-C$_7$) alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like R$_1$ and R$_2$ or R$_2$ and R$_3$ or R$_3$ and R$_4$ or R$_5$ and R$_6$ or R$_6$ and R$_7$ or R$_7$ and R$_8$ or R$_8$ and R$_9$ together with carbon atoms to which they are attached may form a five or a six membered ring, optionally containing one or more double bonds and optionally containing one or more heteroatoms selected from O, N, S and combinations of double bond and heteroatoms; or R$_{11}$ and R$_{12}$ together with carbon atoms to which they are attached may form a three to a six membered ring, optionally containing one or more double bonds and optionally containing one or more heteroatoms selected from O, N, S and combinations of double bond and heteroatoms; R$_{10}$ represents hydrogen, halogen, perhaloalkyl, substituted or unsubstituted groups selected from linear or branched (C$_1$-C$_3$)alkyl and aryl; "n" is an integer ranging from 1 to 8, preferably 1 to 4, wherein the carbon chains which "n" represents may be either linear or branched; and V is an integer ranging from 0 to 2 preferably m is 1 or 2; and Lg is a leaving group as defined earlier and its stereoisomers and its salts.

Novel intermediates of general formula (IX) are represented as given below,

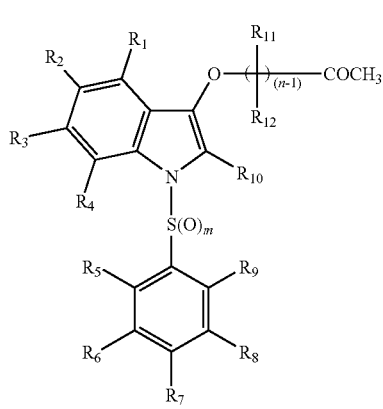

(IX)

wherein R$_1$, R$_2$, R$_3$, R$_4$, R$_5$, R$_6$, R$_7$, R$_8$, R$_9$, R$_{11}$ and R$_{12}$ may be same or different, and represent hydrogen, halogen, perhaloalkyl, hydroxy, thio, amino, nitro, cyano, formyl, amidino, guanidino, substituted or unsubstituted groups selected from linear or branched (C$_1$-C$_{12}$)alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, (C$_1$-C$_{12}$)alkoxy, cyclo(C$_3$-C$_7$) alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl arylalkyl, aralkoxyalkyl, alkylthio, thioalkyl, alkoxycarbonylamino, aralkyloxycarbonylamino, aminocarbonylamino, alkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like R$_1$ and R$_2$ or R$_2$ and R$_3$ or R$_3$ and R$_4$ or R$_5$ and R$_6$ or R$_6$ and R$_7$ or R$_7$ and R$_8$ or R$_8$ and R$_9$ together with carbon atoms to which they are attached may form a five or a sue membered ring, optionally containing one or more double bonds and optionally containing one or more heteroatoms selected from O, N, S and combinations of double bond and heteroatoms; R$_{10}$ represents hydrogen, halogen, perhaloalkyl, substituted or unsubstituted groups selected from linear or branched (C$_1$-C$_3$)alkyl and aryl; "n" is an integer ranging from 1 to 8, preferably 1 to 4, wherein the carbon chains which "n" represents may be either linear or branched; and "m" is an integer ranging from 0 to 2 preferably m is 1 or 2 and its stereoisomers and its salts.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalysts may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino group such as lysine, arginine and the like.

Isotopically labelled compounds of the present invention are useful in drug and/or substrate tissue distribution and target occupancy assays. For example, isotopically labelled compounds are particularly useful in SPECT (single photon emission computed tomography) and in PET (positron emission tomography).

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used. Organic bases such lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, maleic acid, lactic acid, salicyclic acid, citric acid, ascorbic acid, benzene sulfonic acid, p-toluene sulfonic acid, hydroxynaphthoic acid, methane sulfonic acid, malic acid, acetic acid, benzoic acid, succinic acid, palmitic acid, oxalic acid, hydrochloric acid, hydrobromic acid, sulfuric acid, nitric acid and the like in solvents such as water, alcohols, ethers, ethyl acetate, dioxane, DMF or a lower alkyl ketone such as acetone, or the mixtures thereof.

Different polymorphs may be prepared by crystallization of compounds of general formula (I) under different conditions such as different solvents or solvent mixtures in varying proportions for recrystallization, various ways of crystallization such as slow cooling, fast cooling or a very fast cooling or a gradual cooling during crystallization. Also heating the compound, melting the compound and solidification by gradual or fast cooling, heating or melting under vacuum or under inert atmosphere, and cooling under either vacuum or inert atmosphere. Either one or more of the following techniques such as differential scanning calorimeter, powder X-ray diffraction, IR spectroscopy, solid probe NMR spectroscopy and thermal microscopy can identify the polymorphs thus prepared.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

"Therapeutically effective amount" is defined an 'amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein'.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

The affinities of the compound of this invention for the various serotonin receptors are evaluated using standard radioligand binding assays and are described here.

Radioligand Binding Assays for Various 5-HT Receptor Sub-Types:

i) Assay for $5HT_{1A}$

Materials and Methods:
  Receptor source: Human recombinant expressed in HEK-293 cells
  Radioligand: [3H]-8-OH-DPAT (221 Ci/mmol)
  Final ligand concentration—[0.5 nM]
  Reference compound: 8-OH-DPAT
  Positive control: 8-OH-DPAT Incubation Conditions:
  Reactions are carried out in 50 mM TRIS-HCl (pH 7.4) containing 10 mM $MgSO_4$, 0.5 mM EDTA and 0.1% Ascorbic acid at room temperature for 1 hour. The reaction is terminated by rapid vacuum filtration onto glass fiber filters. Radioactivity trapped onto the filters is determined and compared to control values in order to ascertain any interactions of test compound with the $5HT_{1A}$ binding site.

Literature Reference:
Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jml. Pharmacol. 118: 13-23 (1985) with modifications.
Schoeffter P. and Hoyer D. How Selective is GR 43175? Interactions with Functional $5-HT_{1A}$, $5HT_{1B}$, $5-HT_{1C}$, and $5-HT_{1D}$ Receptors. Naunyn-Schmiedeberg's Arch. Pharmac. 340: 135-138 (1989) with modifications.

ii) Assay for $5HT_{1B}$

Materials and Methods:
  Receptor source: Rat striatal membranes
  Radioligand: [$^{125}$I]Iodocyanopindolol (2200 Ci/mmol)
  Final ligand concentration—[0.15 nM]
  Non-specific determinant: Serotonin—[10 µM]
  Reference compound: Serotonin
  Positive control: Serotonin Incubation Conditions:
  Reactions are carried out in 50 mM TRIS-HCl (pH 7.4) containing 60 µM (−) isoproterenol at 37° C. for 60 minutes. The reaction is terminated by rapid vacuum filtration onto glass fiber filters. Radioactivity trapped onto the filters is determined and compared to control values in order to ascertain any interactions of test compound with the $5HT_{1B}$ binding site.

Literature Reference:
Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jml. Pharmacol. 118: 13-23 (1985) with modifications.
Schoeffter P. and Hoyer D. How selective is GR 43175? Interactions with Functional $5-HT_{1A}$, $5HT_{1B}$, $5-HT_{1C}$, and $5-HT_1$ Receptors. Naunyn-Schmiedeberg's Arch. Pharmac. 340: 135-138 (1989) with modifications.

iii) Assay for $5HT_{1D}$

Materials and Methods:
  Receptor source: Human cortex
  Radioligand: [$^3$H] 5-Carboxamidotryptamine (20-70 Ci/mmol)
  Final ligand concentration—[2.0 nM]
  Non-specific determinant: 5-Carboxamidotryptamine (5-CT)-[1.0 µM]
  Reference compound: 5-Carboxamidotryptamine (5-CT)
  Positive control: 5-Carboxamidotryptamine (5-CT)

Incubation Conditions:
  Reactions are carried out in 50 mM TRIS-HCl (pH 7.7) containing 4 mM $CaCl_2$, 100 nM 8-OH-DPAT, 100 nM Mesulergine, 10 uM Pargyline and 0.1% ascorbic acid at 25° C. for 60 minutes. The reaction is terminated by rapid vacuum filtration onto glass fiber filters. Radioactivity trapped onto the filters is determined and compared to control values in order to ascertain any interactions of test compound with the cloned $5HT_{1D}$ binding site.

Literature Reference:
Waeber C, Schoeffter, Palacios J. M. and Hoyer D. Molecular Pharmacology of the $5-HT_{1D}$ Recognition Sites: Radioligand Binding Studies in Human, Pig, and Calf Brain Membranes. Naunyn-Schmiedeberg's Arch. Pharmacol. 337: 595-601 (1988) with modifications.

iv) Assay for $5HT_{2A}$

Materials and Methods:
  Receptor source: Human Cortex
  Radioligand: [$^3$H] Ketanserin (60-90 Ci/mmol)
  Final ligand concentration—[2.0 nM]
  Non-specific determinant: Ketanserin—[3.0 µM]
  Reference compound: Ketanserin
  Positive control: Ketanserin Incubation Conditions:
  Reactions are carried out in 50 mM TRIS-HCl (pH 7.5) at room temperature for 90 minutes. The reaction is terminated by rapid vacuum filtration onto glass fiber filters. Radioactivity trapped onto the filters is determined and compared to control values in order to ascertain any interactions of test compound with the $5HT_{2A}$ binding site.

Literature Reference:
Leysen J. E., Niemegeers C. J., Van Nueten J. M. and Laduron P. M. [$^3$H]Ketanserin: A Selective Tritiated Ligand for Serotonin$_2$ Receptor Binding Sites. Mol. Pharmacol. 21: 301-314 (1982) with modifications.
Martin, G. R. and Humphrey, P. P. A. Classification Review: Receptors for 5-HT: Current Perspectives on Classification and Nomenclature. Neuropharmacol. 33(3/4): 261-273 (1994).

v) Assay for 5HT$_{2C}$

Materials and Methods:
  Receptor source: Pig choroid plexus membranes
  Radioligand: [$^3$H] Mesulergine (50-60 Ci/mmol)
  Final ligand concentration—[1.0 nM]
  Non-specific determinant: Serotonin—[100 nM]
  Reference compound: Mianserin
  Positive control: Mianserin Incubation Conditions:
  Reactions are carried out in 50 mM TRIS-HCl (pH 7.7) containing 4 mM CaCl$_2$ and 0.1% ascorbic acid at 37° C. for 60 minutes. The reaction is terminated by rapid vacuum filtration onto glass fiber filters. Radioactivity trapped onto the filters is determined and compared to control values in order to ascertain any interactions of test compound with the 5HT$_{2C}$ binding site.

Literature Reference:
A. Pazos, D. Hoyer, and J. Palacios. The Binding of Serotonergic Ligands to the Porcine Choroid Plexus: Characterization of a New Type of Serotonin Recognition Site. Eur. Jml. Pharmacol. 106: 539-546 (1985) with modifications.
Hoyer, D., Engel, G., et al. Molecular Pharmacology of 5HT$_1$ and 5-HT$_2$ Recognition Sites in Rat and Pig Brain Membranes: Radioligand Binding Studies with [3H]-5HT, [3H]-8-OH-DPAT, [$^{125}$I]-Iodocyanopindolol, [3H]-Mesulergine and [3H]-Ketanserin. Eur. Jml. Pharmacol. 118: 13-23 (1985) with modifications.

vi) Assay for 5HT$_3$

Materials and Methods:
  Receptor source: N1E-115 cells
  Radioligand: [$^3$H]-GR 65630 (30-70 Ci/mmol)
  Final ligand concentration—[0.35 nM]
  Non-specific determinant: MDL-72222—[1.0 µM]
  Reference compound: MDL-72222
  Positive control: MDL-72222

Incubation Conditions:
  Reactions are carried out in 20 mM HEPES (pH 7.4) containing 150 mM NaCl at 25° C. for 60 minutes. The reaction is terminated by rapid vacuum filtration onto glass fiber filters. Radioactivity trapped onto the filters is determined and compared to control values in order to ascertain any interactions of test compound with the 5HT$_3$ binding site.

Literature Reference:
Lummis S. C. R., Kilpatrick G. J. Characterization of 5HT$_3$ Receptors in intact N1E-115 Neuroblastoma Cells. Eur. Jml. Pharmacol. 189: 223-227 (1990) with modifications.
Hoyer D. and Neijt H. C. Identification of Serotonin 5-HT$_3$ Recognition Sites in Membranes of N1E-115 Neuroblastoma Cells by Radioligand Binding. Mol. Pharmacol. 33: 303 (1988).
Tyers M. B. 5-HT$_3$ Receptors and the Therapeutic Potential of 5HT$_3$ Receptor Antagonists. Therapie. 46:431-435 (1991).

vii) Assay for 5HT$_4$

Materials and Methods:
  Receptor source: Guinea pig striatal membranes
  Radioligand: [$^3$H] GR-113808 (30-70 Ci/mmol)
  Final ligand concentration—[0.2 nM]
  Non-specific determinant: Serotonin (5-HT)-[30 µM]
  Reference compound: Serotonin (5-HT)
  Positive control: Serotonin (5-HT)

Incubation Conditions:
  Reactions are carried out in 50 mM HEPES (pH 7.4) at 370C for 60 minutes. The reaction is terminated by rapid vacuum filtration onto glass fiber filters. Radioactivity trapped onto the filters is determined and compared to control values in order to ascertain any interactions of test compound with the 5HT$_4$ binding site.

Literature Reference:
Grossman Kilpatrick, C, et al. Development of a Radioligand Binding Assay for 5HT$_4$ Receptors in Guinea Pig and Rat Brain. Brit. J Pharmco. 109: 618-624 (1993).

viii) Assay for 5HT$_{5A}$

Materials and Methods:
  Receptor source: Human recombinant expressed in HEK 293 cells
  Radioligand: [$^3$H] LSD (60-87 Ci/mmol)
  Final ligand concentration—[1.0 nM]
  Non-specific determinant: Methiothepin mesylate—[1.0 µM]
  Reference compound: Methiothepin mesylate
  Positive control: Methiothepin mesylate Incubation Conditions:
  Reactions are carried out in 50 mM TRIS-HCl (pH 7.4) containing 10 mM MgSO$_4$ and 0.5 mM EDTA at 37° C. for 60 minutes. The reaction is terminated by rapid vacuum filtration onto glass fiber filters. Radioactivity trapped onto the filters is determined and compared to control values in order to ascertain any interactions of test compound with the cloned 5HT$_{5A}$ binding site.

Literature Reference:
Rees S., et al. FEBS Letters, 355: 242-246 (1994) with modifications ix) Assay for 5HT$_6$ Materials and Methods:
  Receptor source: Human recombinant expressed in HEK293 cells
  Radioligand: [$^3$H] LSD (60-80 Ci/mmol)
  Final ligand concentration—[1.5 nM]
  Non-specific determinant: Methiothepin mesylate—[0.1 µM]
  Reference compound: Methiothepin mesylate
  Positive control: Methiothepin mesylate Incubation Conditions:
  Reactions are carried out in 50 mM TRIS-HCl (pH 7.4) containing 10 mM MgCl$_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin—5HT$_6$-binding site.

Literature Reference:
Monsma F. J. Jr., et al., Molecular Cloning and Expression of Novel Serotonin Receptor with High Affinity for Tricyclic Psychotropic Drugs. Mol. Pharmacol. (43): 320-327 (1993).

x) Assay for 5-HT$_7$

Materials and Methods:
  Receptor source: Human recombinant expressed in CHO cells
  Radioligand: [$^3$H] LSD (60-80 Ci/mmol)
  Final ligand concentration—[2.5 nM]

Non-specific determinant: 5-Carboxamidotryptamine (5-CT)-[0.1 µM]
  Reference compound: 5-Carboxamidotryptamine
  Positive control: 5-Carboxamidotryptamine Incubation Conditions:

Reactions are earned out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin—$5HT_7$-binding site.

Literature Reference:

Y. Shen, E. Monsma, M. Metcalf, P. Jose, M Hamblin, D. Sibley, Molecular Cloning and Expression of a 5-hydroxytryptamine-7 Serotonin Receptor Subtype. J. Biol. Chem. 268: 18200-18204.

The following description illustrates the method of preparation of variously substituted compounds of general formula (I), according to the methods described herein. These are provided by the way of illustration only and therefore should not be construed to limit the scope of the invention.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. 1H NMR spectra were recorded at 200 MHz on a Bruker instrument. Deuterated chloroform (99.8% D) was used as solvent. TMS was used as internal reference standard. Chemical shift values are expressed in are reported in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Description 1: General Procedure for the Preparation of Monoperphthalic Acid (D 1)

To the mixture containing phthalic anhydride (2.22 g, 0.015 mole) and diethyl ether (25 mL), hydrogen peroxide solution (3.4 g; 0.03 moles; as 30% aqueous solution) was added and the reaction mixture was stirred at 25° C. to dissolve the anhydride. The reaction mixture was transferred to a separating funnel, ether layer was separated and aqueous layer was extracted with ether (3×10 mL). Combined ether extracts are dried over sodium sulfate and this solution of monoperphthalic acid was used.

Description 2: 1-Benzenesulfonyl-2-phenyl-1H-indole (D 2)

Route I:

In a three-necked round bottom flask equipped with pressure equalizing funnel, sodium hydride (0.6 g of 50% in mineral oil; 0.0125 mole) and DMF (8 mL) were taken. 2-Phenyl-1H-indole (0.01 mole) was added slowly at 0° C. and the reaction mixture was stirred well. Then it was warmed to 25° C. and stirring was continued for one hour. Afterwards, the reaction mixture was cooled and Benzenesulfonyl chloride (2.1 g; 0.012 mole in 5 mL) was added slowly from the pressure equalizing funnel over minutes, and further stirred at 25° C. for 3 hours. After completion of reaction (TLC), the reaction mixture was poured in in cold water and the product was extracted in ethyl acetate (2×25 mL). The combined organic extracts were washed with water, followed by brine, dried over anhydrous sodium sulfate and the product was isolated by distillation under reduced pressure. The product usually was an oily compound, which was as such used for the next step.

The crude residue was purified by silica gel column chromatography using 30% methanol in ethyl acetate as a mobile phase, to obtain the title compound, which was identified by IR, NMR and mass spectral analyses.

Route II:

Instead of sodium hydride (0.6 g of 50% suspension in mineral oil; 0.0125 mole), either sodium hydroxide (0.03 moles) or potassium hydroxide (0.03 moles) was taken and similar procedure was followed.

Various substituted indoles were treated with substituted phenylsulfonylchloride as described above. These compounds were identified by IR, NMR and mass spectral analyses. Following is the partial list of such compounds:

List-1:

| | Description | Mass ion $(M + H)^+$ |
|---|---|---|
| D2 | 1-Benzenesulfonyl-2-phenyl-1H-indole | 334 |
| D3 | 1-Benzenesulfonyl-2-phenyl-5-methoxy-1H-indole | 364 |
| D4 | 1-Benzenesulfonyl-2-phenyl-5-methyl-1H-indole | 348 |
| D5 | 1-Benzenesulfonyl-5-bromo-2-phenyl-1H-indole | 412/414 |
| D6 | 1-Benzenesulfonyl-5-chloro-2-phenyl-1H-indole | 368/370 |
| D7 | 1-Benzenesulfonyl-5-fluoro-2-phenyl-1H-indole | 352 |
| D8 | 1-(2'-Bromobenzenesulfonyl)-2-phenyl-1H-indole | 412/414 |
| D9 | 1-(4'-Methylbenzenesulfonyl)-5-fluoro-2-phenyl-1H-indole | 366 |
| D10 | 1-(4'-Methylbenzenesulfonyl)-5-chloro-2-phenyl-1H-indole | 382/384 |
| D11 | 1-(2'-Bromo-4'-methylbenzenesulfonyl)-2-Phenyl-1H-indole | 426/428 |
| D12 | 1-(2'-Bromo-4'-isopropylbenzenesulfonyl)-2-phenyl-1H-indole | 454/456 |
| D13 | 1-(4'-Fluorobenzenesulfonyl)-5-chloro-2-phenyl-1H-indole | 386/3838 |
| D14 | 1-Benzenesulfonyl-2-methyl-1H-indole | 272 |
| D15 | 1-Benzenesulfonyl-2-methyl-5-methoxy-1H-indole | 302 |
| D16 | 1-Benzenesulfonyl-2,5-dimethyl-1H-indole | 286 |
| D17 | 1-Benzenesulfonyl-5-bromo-2-methyl-1H-indole | 350/352 |
| D18 | 1-Benzenesulfonyl-5-chloro-2-methyl-1H-indole | 306/308 |
| D19 | 1-Benzenesulfonyl-5-fluoro-2-methyl-1H-indole | 290 |
| D20 | 1-(2'-Bromobenzenesulfonyl)-2-methyl-1H-indole | 350/352 |
| D21 | 1-(4'-Methylbenzenesulfonyl)-5-fluoro-2-methyl-1H-indole | 304 |
| D22 | 1-(4'-Methylbenzenesulfonyl)-5-chloro-2-methyl-1H-indole | 320/322 |
| D23 | 1-(2'-Bromo-4'-methylbenzenesulfonyl)-2-methyl-1H-indole | 364/366 |
| D24 | 1-(2'-Bromo-4'-isopropylbenzenesulfonyl)-2-methyl-1H-indole | 392/394 |
| D25 | 1-(4'-Fluorobenzenesulfonyl)-5-chloro-2-methyl-1H-indole | 324 |

Description 26: 1-Benzenesulfonyl-2-phenyl-1H-indol-3-ol (D 26)

Route 1:

1-Benzenesulfonyl-2-phenyl-1H-indole (D1) (0.01 mole) was dissolved in glacial acetic acid (15 mL) and was transferred to three-necked flask. To this mixture monoperphphtalate (0.02 moles of 50% suspension) solution in ether was added and 3 stirred at 25° C. for 3 hours. After the completion of reaction, the volatile substances were removed under reduced pressure. The residue was added ethyl acetate:water (1:1) mixture, followed by sodium bicarbonate. The organic layer was separated and the aqueous layer was extracted with ethyl acetate (3×20 mL). The combined organic extracts were washed with brine and the ethyl acetate was distilled off to obtain the crude intermediate. This intermediate was taken as such to the next step without purification.

Route 2:

Alternatively 1-Benzenesulfonyl-1H-indol-3-ol derivatives can also be obtained as reported in the Heterocycles, Vol. 30, No. 1, 1990, by reacting corresponding benzenesulfonylindoles with magnesium monoperphthalate.)

Various other derivatives of general formula (II) were prepared as described above. These compounds were identified by IR, NMR and mass spectral analyses. Following is the partial list of such compounds.

List-2:

| | Description | Mass ion (M + H)+ |
|---|---|---|
| D26 | 1-Benzenesulfonyl-2-phenyl-1H-indol-3-ol | 350 |
| D27 | 1-Benzenesulfonyl-2-phenyl-5-methoxy-1H-indol-3-ol | 380 |
| D28 | 1-Benzenesulfonyl-2-phenyl-5-methyl-1H-indol-3-ol | 364 |
| D29 | 1-Benzenesulfonyl-5-bromo-2-phenyl-1H-indol-3-ol | 428/430 |
| D30 | 1-Benzenesulfonyl-5-chloro-2-phenyl-1H-indol-3-ol | 384/386 |
| D31 | 1-Benzenesulfonyl-5-fluoro-2-phenyl-1H-indol-3-ol | 368 |
| D32 | 1-(2'-Bromobenzenesulfonyl)-2-phenyl-1H-indol-3-ol | 428/430 |
| D33 | 1-(4'-Methylbenzenesulfonyl)-5-fluoro-2-phenyl-1H-indol-3-ol | 382 |
| D34 | 1-(4'-Methylbenzenesulfonyl)-5-chloro-2-phenyl-1H-indol-3-ol | 398/400 |
| D35 | 1-(2'-Bromo-4'-methylbenzenesulfonyl)-2-phenyl-1H-indol-3-ol | 442/444 |
| D36 | 1-(2'-Bromo-4'-isopropylbenzenesulfonyl)-2-phenyl-1H-indol-3-ol | 470/472 |
| D37 | 1-(4'-Fluorobenzenesulfonyl)-5-chloro-2-phenyl-1H-indol-3-ol | 402/404 |
| D38 | 1-Benzenesulfonyl-2-methyl-1H-indol-3-ol | 288 |
| D39 | 1-Benzenesulfonyl-2-methyl-5-methoxy-1H-indol-3-ol | 318 |
| D40 | 1-Benzenesulfonyl-2,5-dimethyl-1H-indol-3-ol | 302 |
| D41 | 1-Benzenesulfonyl-5-bromo-2-methyl-1H-indol-3-ol | 366/368 |
| D42 | 1-Benzenesulfonyl-5-chloro-2-methyl-1H-indol-3-ol | 322/324 |
| D43 | 1-Benzenesulfonyl-5-fluoro-2-methyl-1H-indol-3-ol | 306 |
| D44 | 1-(2'-Bromobenzenesulfonyl)-2-methyl-1H-indol-3-ol | 366/368 |
| D45 | 1-(4'-Methylbenzenesulfonyl)-5-fluoro-2-methyl-1H-indol-3-ol | 320 |
| D46 | 1-(4'-Methylbenzenesulfonyl)-5-chloro-2-methyl-1H-indol-3-ol | 336/338 |
| D47 | 1-(2'-Bromo-4'-methylbenzenesulfonyl)-2-methyl-1H-indol-3-ol | 380/382 |
| D48 | 1-(2'-Bromo-4'-isopropylbenzenesulfonyl)-2-methyl-1H-indol-3-ol | 408/410 |
| D49 | 1-(4'-Fluorobenzenesulfonyl)-5-chloro-2-methyl-1H-indol-3-ol | 340/342 |

Description 50: 1-(3-Hydroxyindol-1-yl)ethanone (D 50)

According to the methods given in literature following N-acetylindoxyls were prepared and listed as below. These compounds were identified by IR, NMR and mass spectral analyses.

List-3:

| | Description | Mass ion (M + H)+ |
|---|---|---|
| D50 | 1-(3-Hydroxyindol-1-yl)ethanone | 176 |
| D51 | 1-(5-Bromo-3-hydroxyindol-1-yl)ethanone | 254/256 |
| D52 | 1-(5-Chloro-3-hydroxyindol-1-yl)ethanone | 210/212 |
| D53 | 1-(5-Fluoro-3-hydroxyindol-1-yl)ethanone | 194 |
| D54 | 1-(6-Chloro-3-hydroxyindol-1-yl)ethanone | 210/212 |
| D55 | 1-(3-Hydroxy-5-methoxyindol-1-yl)ethanone | 206 |
| D56 | 1-(5,7-Dibromo-3-hydroxyindol-1-yl)ethanone | 332/334/336 |
| D57 | 1-(6-Chloro-5-methoxy-3-hydroxyindol-1-yl)ethanone | 240/242 |
| D58 | 1-(6-Chloro-5-fluoro-3-hydroxyindol-1-yl)ethanone | 228/230 |
| D59 | 1-(6-Bromo-5-methoxy-3-hydroxyindol-1-yl)ethanone | 284/286 |
| D60 | 1-(6-Bromo-5-fluoro-3-hydroxyindol-1-yl)ethanone | 272/274 |
| D61 | 1-(4-Chloro-5-fluoro-3-hydroxyindol-1-yl)ethanone | 228/230 |
| D62 | 1-(4-Methoxy-5-fluoro-3-hydroxyindol-1-yl)ethanone | 224 |
| D63 | 1-(3-Hydroxy-2-phenylindol-1-yl)ethanone | 252 |
| D64 | 1-(5-Bromo-3-hydroxy-2-phenylindol-1-yl)ethanone | 330/332 |
| D65 | 1-(5-Chloro-3-hydroxy-2-phenylindol-1-yl)ethanone | 286/288 |
| D66 | 1-(5-Fluoro-3-hydroxy-2-phenylindol-1-yl)ethanone | 270 |
| D67 | 1-(6-Chloro-3-hydroxy-2-phenylindol-1-yl)ethanone | 286/288 |
| D68 | 1-(3-Hydroxy-5-methoxy-2-phenylindol-1-yl)ethanone | 282 |
| D69 | 1-(5,7-Dibromo-3-hydroxy-2-phenylindol-1-yl)ethanone | 408/410/412 |
| D70 | 1-(6-Chloro-5-methoxy-3-hydroxy-2-phenylindol-1-yl)ethanone | 316/318 |
| D71 | 1-(6-Chloro-5-fluoro-3-hydroxy-2-phenylindol-1-yl)ethanone | 304 |
| D72 | 1-(6-Bromo-5-methoxy-3-hydroxy-2-phenylindol-1-yl)ethanone | 360/362 |
| D73 | 1-(6-Bromo-5-fluoro-3-hydroxy-2-phenylindol-1-yl)ethanone | 348/350 |
| D74 | 1-(4-Chloro-5-fluoro-3-hydroxy-2-phenylindol-1-yl)ethanone | 304/306 |
| D75 | 1-(4-Methoxy-5-fluoro-3-hydroxy-2-Phenylindol-1-yl)ethanone | 300 |
| D76 | 1-(3-Hydroxy-2-methylindol-1-yl)ethanone | 190 |
| D77 | 1-(5-Bromo-3-hydroxy-2-methylindol-1-yl)ethanone | 268/270 |
| D78 | 1-(5-Chloro-3-hydroxy-2-methylindol-1-yl)ethanone | 224 |
| D79 | 1-(5-Fluoro-3-hydroxy-2-methylindol-1-yl)ethanone | 208 |
| D80 | 1-(6-Chloro-3-hydroxy-2-methylindol-1-yl)ethanone | 224/226 |
| D81 | 1-(3-Hydroxy-5-methoxy-2-methylindol-1-yl)ethanone | 220 |
| D82 | 1-(5,7-Dibromo-3-hydroxy-2-methylindol-1-yl)ethanone | 346/348/350 |
| D83 | 1-(6-Chloro-5-methoxy-3-hydroxy-2-methylindol-1-yl)ethanone | 254/256 |
| D84 | 1-(6-Chloro-5-fluoro-3-hydroxy-2-methylindol-1-yl)ethanone | 242/244 |
| D85 | 1-(6-Bromo-5-methoxy-3-hydroxy-2-methylindol-1-yl)ethanone | 298/300 |
| D86 | 1-(6-Bromo-5-fluoro-3-hydroxy-2-methylindol-1-yl)ethanone | 286/288 |
| D87 | 1-(4-Chloro-5-fluoro-3-hydroxy-2-methylindol-1-yl)ethanone | 242/244 |
| D88 | 1-(4-Methoxy-5-fluoro-3-hydroxy-2-methylindol-1-yl)ethanone | 238 |

Description 89: [2-(1-Acetyl-1H-indol-3-yloxy)ethyl]dimethylamine (D 89)

According to the methods given in literature (U.S. Pat. No. 3,860,608) following derivatives were prepared and listed as below. These compounds were identified by IR, NMR and mass spectral analyses. The following procedure also describes the method of synthesis of the same.

1-Acetyl-3-indoxyl (0.015 mole), was taken in three necked flask along with potassium carbonate (0.030 mole); tetrahydrofuran (ca 15 mL) and N,N-dimethylaminoethyl chloride (ca 15% solution in toluene; 0.015 mole) and the mixture was refluxed for 3 hours. Another, lot of N,N-dimethylaminoethyl chloride (ca 15% solution in toluene; 0.015 mole) was added and the reaction mixture was refluxed for further 3 hours. The reaction mixture was cooled to 25° C. and filtered. The filtrate was washed with water and brine; dried over sodium sulfate; organic solvents were removed under reduced pressure and the residue was purified by column chromatography, on silica gel; using hexane (100%) to triethylamine:ethyl acetate (2:98) gradual gradient as mobile phase, to obtain the compound of general formula (I) as thick oil, which was identified by IR, NMR and mass spectral analyses. The final desired compound of general formula (X) can be further purified by preparation of their acid addition salts.

List-4:

|  | Description | Mass ion (M + H)+ |
|---|---|---|
| D89 | [2-(1-Acetyl-1H-Indol-3-yloxy)ethyl]dimethylamine | 247 |
| D90 | [2-(1-Acetyl-2-Phenyl-1H-indol-3-yloxy)ethyl]dimethylamine | 323 |
| D91 | [2-(1-Acetyl-2-Methyl-1H-indol-3-yloxy)ethyl]dimethylamine | 261 |
| D92 | [2-(1-Acetyl-5-Bromo-1H-indol-3-yloxy)ethyl]dimethylamine | 325/327 |
| D93 | [2-(1-Acetyl-5-Bromo-2-phenyl-1H-indol-3-yloxy)ethyl]dimethylamine | 401/403 |
| D94 | [2-(1-Acetyl-5-Bromo-2-methyl-1H-indol-3-yloxy)ethyl]dimethylamine | 339/341 |
| D95 | [2-(1-Acetyl-5-Chloro-1H-indol-3-yloxy)ethyl]dimethylamine | 281/283 |
| D96 | [2-(1-Acetyl-5-Chloro-2-phenyl-1H-indol-3-yloxy)ethyl]dimethylamine | 357/359 |
| D97 | [2-(1-Acetyl-5-Chloro-2-methyl-1H-indol-3-yloxy)ethyl]dimethylamine | 295/297 |
| D98 | [2-(1-Acetyl-6-Chloro-1H-indol-3-yloxy)ethyl]dimethylamine | 281/283 |
| D99 | [2-(1-Acetyl-6-Chloro-2-phenyl-1H-indol-3-yloxy)ethyl]dimethylamine | 357/359 |
| D100 | [2-(1-Acetyl-6-Chloro-2-methyl-1H-indol-3-yloxy)ethyl]dimethylamine | 295/297 |
| D101 | [2-(1-Acetyl-5,7-Dichloro-1H-indol-3-yloxy)ethyl]dimethylamine | 315/317/319 |
| D102 | [2-(1-Acetyl-5,7-Dichloro-2-phenyl-1H-indol-3-yloxy)ethyl]dimethylamine | 391/393/395 |
| D103 | [2-(1-Acetyl-5,7-Dichloro-2-methyl-1H-indol-3-yloxy)ethyl]dimethylamine | 329/331/333 |
| D104 | [2-(1-Acetyl-5,7-Dibromo-1H-indol-3-yloxy)ethyl]dimethylamine | 403/405/407 |
| D105 | [2-(1-Acetyl-5,7-Dibromo-2-phenyl-1H-indol-3-yloxy)ethyl]dimethylamine | 479/481/483 |
| D106 | [2-(1-Acetyl-5,7-Dibromo-2-methyl-1H-indol-3-yloxy)ethyl]dimethylamine | 417/419/421 |
| D107 | [2-(1-Acetyl-7-Bromo-5-chloro-1H-indol-3-yloxy)ethyl]dimethylamine | 359/361 |
| D108 | [2-(1-Acetyl-7-Bromo-5-chloro-2-phenyl-1H-indol-3-yloxy)ethyl]dimethylamine | 435/437 |
| D109 | [2-(1-Acetyl-7-Bromo-5-chloro-2-methyl-1H-indol-3-yloxy)ethyl]dimethylamine | 373/375 |
| D110 | [2-(1-Acetyl-5-Methoxy-1H-indol-3-yloxy)ethyl]dimethylamine | 277 |
| D111 | [2-(1-Acetyl-5-Methoxy-2-phenyl-1H-indol-3-yloxy)ethyl]dimethylamine | 353 |
| D112 | [2-(1-Acetyl-5-Methoxy-2-methyl-1H-indol-3-yloxy)ethyl]dimethylamine | 291 |

Description 113: [2-(1H-indol-3-yloxy)ethyl]dimethylamine (D 113)

According to the methods given in literature (U.S. Pat. No. 3,860,608) the above derivatives were deacetylated. These compounds were identified by IR, NMR and mass spectral analyses. The following procedure also describes the method of synthesis of above compounds,

[2-(1-Acetyl-1H-indol-3-yloxy)ethyl]dimethylamine (0.015 mole), was taken in three necked flask along with sodium hydroxide (0.022 mole), water (ca 15 mL) and methanol (ca 15 mL). The reaction mixture was refluxed for 30 minutes to 2 hours. The reaction mixture was cooled to 25° C. and poured on to ice-cold water. The compound was extracted with ethyl acetate (3×20 mL), the combined organic extracts were washed with water and brine; dried over sodium sulfate; organic solvents were removed under reduced pressure and the residue was purified by column chromatography, on silica gel; using hexane (100%) to triethylamine:ethyl acetate (2:98) gradual gradient as mobile phase, to obtain the compound of general formula (I) as thick oil, which was identified by IR, NMR and mass spectral analyses. The final desired compound of general formula (IV) can be further purified by preparation of their acid addition salts.

List-5:

|  | Description | Mass ion (M + H)+ |
|---|---|---|
| D113 | [2-(1H-Indol-3-yloxy)ethyl]dimethylamine | 205 |
| D114 | [2-(2-Phenyl-1H-indol-3-yloxy)ethyl]dimethylamine | 281 |
| D115 | [2-(2-Methyl-1H-indol-3-yloxy)ethyl]dimethylamine | 219 |
| D116 | [2-(5-Bromo-1H-indol-3-yloxy)ethyl]dimethylamine | 283/285 |
| D117 | [2-(5-Bromo-2-phenyl-1H-indol-3-yloxy)ethyl]dimethylamine | 359/361 |
| D118 | [2-(5-Bromo-2-methyl-1H-indol-3-yloxy)ethyl]dimethylamine | 297/298 |
| D119 | [2-(5-Chloro-1H-indol-3-yloxy)ethyl]dimethylamine | 239/241 |
| D120 | [2-(5-Chloro-2-phenyl-1H-indol-3-yloxy)ethyl]dimethylamine | 315/317 |
| D121 | [2-(5-Chloro-2-methyl-1H-indol-3-yloxy)ethyl]dimethylamine | 253/255 |
| D122 | [2-(6-Chloro-1H-indol-3-yloxy)ethyl]dimethylamine | 239/241 |
| D123 | [2-(6-Chloro-2-phenyl-1H-indol-3-yloxy)ethyl]dimethylamine | 315/317 |
| D124 | [2-(6-Chloro-2-methyl-1H-indol-3-yloxy)ethyl]dimethylamine | 253/255 |

-continued

| Description | Mass ion (M + H)+ |
|---|---|
| D125 [2-(5,7-Dichloro-1H-indol-3-yloxy)ethyl]dimethylamine | 273/275/277 |
| D126 [2-(5,7-Dichloro-2-phenyl-1H-indol-3-yloxy)ethyl]dimethylamine | 349/351/353 |
| D127 [2-(5,7-Dichloro-2-methyl-1H-indol-3-yloxy)ethyl]dimethylamine | 287/289/291 |
| D128 [2-(5,7-Dibromo-1H-indol-3-yloxy)ethyl]dimethylamine | 361/363/365 |
| D129 [2-(5,7-Dibromo-2-phenyl-1H-indol-3-yloxy)ethyl]dimethylamine | 437/439/441 |
| D130 [2-(5,7-Dibromo-2-methyl-1H-indol-3-yloxy)ethyl]dimethylamine | 375/377/379 |
| D131 [2-(7-Bromo-5-chloro-1H-indol-3-yloxy)ethyl]dimethylamine | 317/319/321 |
| D132 [2-(7-Bromo-5-chloro-2-phenyl-1H-indol-3-yloxy)ethyl]dimethylamine | 393/395/397 |
| D133 [2-(7-Bromo-5-chloro-2-methyl-1H-indol-3-yloxy)ethyl]dimethylamine | 331/333/335 |
| D134 [2-(5-Methoxy-1H-indol-3-yloxy)ethyl]dimethylamine | 235 |
| D135 [2-(5-Methoxy-2-phenyl-1H-indol-3-yloxy)ethyl]dimethylamine | 311 |
| D136 [2-(5-Methoxy-2-methyl-1H-indol-3-yloxy)ethyl]dimethylamine | 249 |

Example-1

[2-(1-(4'-Bromobenzenesulfonyl)-1H-indol-3-yloxy)ethyl]dimethylamine

Sodium hydride (60% in mineral oil, 16.5 mmoles) was stirred with dimethyl formamide (ca 8 mL) in a ice-cooled, three necked round bottom flask. A solution of [2-(1H-indol-3-yloxy)ethyl]dimethylamine (15 mmole), in dimethyl formamide (ca 5 mL) was then added dropwise to this cooled suspension of sodium hydride. After the addition was complete, the reaction mixture was allowed to attain the room temperature (25° C.). After about one hour of stirring at 25° C., a solution of 4-Bromobenzenesulfonyl chloride (18 mmole) was added dropwise to this solution. The reaction was further stirred at 25° C. for next 3-4 hours. After the completion of reaction (TLC), reaction mixture was poured on the ice cooled water and extracted by Ethyl acetate (3×20 mL). The combined organic extract was washed with water and brine, dried over sodium sulphate and the volatiles were evaporated under vacuum to get the product as a thick dark oil. The residue was purified by column chromatography, on silica gel; using hexane (100%) to triethylamine:ethyl acetate (2:98) gradual gradient as mobile phase, to obtain the compound of general formula (I) as thick oil, which was identified by IR, NMR and mass spectral analyses. The final desired compound of general formula (I) can be further purified by preparation of their acid addition salts. Melting range (° C.): Isolated as oil; Mass (m/z): 423, 425 (M+H)+; IR spectra (cm$^{-1}$): 1150 (SO$_2$); $^1$H-NMR (ppm): 2.40 (s, 6H); 2.83-2.88 (t, 2H, J=5.4 Hz); 4.11-4.16 (t, 2H, J=5.4 Hz); 6.87 (s, 1H); 7.19-7.38 (m, 3H); 7.50-7.67 (m, 4H); 7.95-7.99 (d, 1H).

Example-2

[2-(1-(2'-Bromo-4'-methylbenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150 (SO$_2$), 2900 (C—H stretch); Mass (m/z): 437, 439 (M+H)+; $^1$H-NMR (ppm): 2.33 (s, 3H); 2.38 (s, 6H); 2.80-2.85 (t, 2H, J=5.4 Hz); 4.12-4.17 (t, 2H, J=5.4 Hz); 7.13 (s, 1H); 7.20-7.26 (m, 3H); 7.47 (d, 1H); 7.57-7.58 (m, 1H); 7.77-7.81 (m, 2H)

Example-3

[2-(1-(2*-Bromobenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150 (SO$_2$), 2900 (C—H stretch); Mass (m/z): 423, 425 (M+H)+; $^1$H-NMR (ppm): 2.36 (s, 6H); 2.77-2.83 (t, 2H, J=5.4 Hz); 4.11-4.16 (t, 2H, J=5.4 Hz); 7.13 (s, 1H); 7.18-7.41 (m, 4H); 7.59-7.84 (m, 4H)

Example-4

[2-(1-(4'-Fluorobenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150 (SO$_2$), 2900 (C—H stretch); Mass (m/z): 363 (M+H)+; $^1$H-NMR (ppm): 2.38 (s, 6H); 2.80-2.86 (t, 2H, J=5.4 Hz); 4.09-4.15 (t, 2H, J=5.4 Hz); 6.88 (s, 1H); 7.01-7.10 (m, 2H); 7.22-738 (m, 2H); 7.51-7.55 (dd, 1H); 7.78-7.85 (m, 2H); 7.96-8.00 (dd, 1H)

Example-5

[2-(1-(4'-Chlorobenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150 (SO$_2$), 2900 (C—H stretch); Mass (m/z): 379.1 (M+H)+; $^1$H-NMR (ppm): 2.36 (s, 6H); 2.79-2.82 (t, 2H, J=5.4 Hz); 4.07-4.13 (t, 2H, J=5.4 Hz); 6.87 (s, 1H); 7.18-7.38 (m, 4H); 7.52-7.56 (dd, 1H); 7.51-7.55 (dd, 1H); 7.69-7.76 (d, 2H); 7.95-7.99 (d, 1H)

Example-6

[2-(1-(4'-Methylbenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150 (SO$_2$), 2900 (C—H stretch); Mass (m/z): 359.3 (M+H)$^+$

Example-7

[2-(1-(4'-Isopropylbenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1155; Mass (m/z): 387 (M+H)$^+$;

Example-8

[2-(1-(2'-Bromo-4'-methoxybenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 453, 455 (M+H)$^+$;

Example-9

[2-(1-(Benzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1152; Mass (m/z): 345 (M+H)$^+$;

Example-10

[2-(1-(3',4'-Dimethoxybenzenesulfonyl)-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 405 (M+H)$^+$;

Example-11

[2-(1-Benzenesulfonyl)-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 421.5 (M+H)$^+$;

Example-12

[2-(1-(4'-Fluorobenzenesulfonyl)-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 439.4 (M+H)$^+$;

Example-13

[2-(1-4'-Bromobenzenesulfonyl)-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 499, 501 (M+H)$^+$;

Example-14

[2-(1-(4'-Isopropylbenzenesulfonyl)-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1155; Mass (m/z): 463.4 (M+H)$^+$;

Example-15

[2-(1-(3',4'-Dimethoxybenzenesulfonyl)-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1153; Mass (m/z): 481.3 (M+H)$^+$;

Example-16

[2-(1-(4'-Methylbenzenesulfonyl)-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$); 1154; Mass (m/z): 435.3 (M+H)$^+$;

Example-17

[2-(1-(4'-Chlorobenzenesulfonyl)-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 455, 457 (M+H)$^+$;

Example-18

[2-(1-(2'-Bromo-4'-Methylbenzenesulfonyl)-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1152; Mass (m/z): 513, 515 (M+H)$^+$;

Example-19

[2-(1-(2'-Bromo-4'-Methoxybenzenesulfonyl)-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1150; Mass (m/z): 529, 531 (M+H)$^+$;

Example-20

[2-(1-(2'-Bromobenzenesulfonyl)-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1154; Mass (m/z): 499, 501 (M+H)$^+$;

Example-21

[2-(1-Benzenesulfonyl)-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1155; Mass (m/z): 359.3 (M+H)$^+$;

Example-22

[2-(1-(4'-fluorobenzenesulfonyl)-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z): 377.3 (M+H)$^+$;

Example-23

[2-(1-(4'-Bromobenzenesulfonyl)-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1150; Mass (m/z); 437, 439 (M+H)$^+$;

Example-24

[2-(1-(4'-Isopropylbenzenesulfonyl)-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1152; Mass (m/z): 401.4 (M+H)$^+$;

Example-25

[2-(1-(3',4'-Dimethoxybenzenesulfonyl)-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1154; Mass (m/z): 419.5 (M+H)$^+$;

Example-26

[2-(1-(2'-Bromobenzenesulfonyl)-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1155; Mass (m/z): 437, 439 (M+H)$^+$;

Example-27

[2-(1-(2'-Bromo-4'-Methylbenzenesulfonyl)-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1150; Mass (m/z): 451, 453 (M+H)$^+$;

Example-28

[2-(1-(2'-Bromo-4'-methoxybenzenesulfonyl)-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1150; Mass (m/z): 467, 469 (M+H)$^+$;

Example-29

[2-(1-(4'-Chlorobenzenesulfonyl)-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1154; Mass (m/z): 394, 396 (M+H)$^+$;

Example-30

[2-(1-(4'-Isopropylbenzenesulfonyl)-5-bromo-1H-indol-3-yloxy)ethyl]dimethylamine Using essentially the general procedure described in example 1 and some non-critical variations, the above derivative was prepared. Melting range (° C.): 105-107; IR spectra (cm$^{-1}$): 1174.57 (SO$_2$), 2962, 2967 (C—H Stretching); Mass (m/z): 465, 467.3 (M+H)$^+$; $^1$H-NMR (ppm): 1.17-1.2 (d, 6H,); 2.2 (s, 6H); 2.78 (t, 2H, J=5.4 Hz); 2.81 (septet, 1H); 4.06-4.11 (t, 2H, J=5.4 Hz); 6.918 (s, 1H); 7.22-7.26 (d, 2H); 7.39-7.44 (dd, 1H); 7δ-7.9 (m, 4H);

Example-31

[2-(1-(2'-Bromobenzenesulfonyl)-5-bromo-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1178.49 (SO$_2$); Mass (m/z): 501, 503, 505 (M+H)$^+$; $^1$H-NMR (ppm): 2.3 (s, 6H); 2.74 (t, 2H); 4.02-4.08 (t, 2H); 7.04 (s, 1H); 7.29-7.35 (m, 3H); 7.52-7.81 (m, 4H)

Example-32

[2-(1-Benzenesulfonyl)-5-bromo-1H-indol-3-yloxy)ethyl]dimethylamine

Using essentially the general procedure described in example 1 and some non-critical variations, the above derivative was prepared. Melting range (° C.): Isolated as oil; 224-

226 (HCl salt); IR spectra (cm$^{-1}$): 1176.32 (SO$_2$); Mass (m/z): 423, 425 (M+H)$^+$; $^1$H-NMR (ppm): D3.02 (s, 6H); 3.65-3.67 (t, 2H, J=5.4 Hz); 4.43-4.47 (t, 2H, J=5.4 Hz); 7.37 (s, 1H); 7.48-7.64, (m, 4H); 7.78-7.79 (d, 1H); 7.94-7.99 (m, 3H)

Example-33

[2-(1-(4'-Fluorobenzenesulfonyl)-5-bromo-1H-indol-3-yloxy)ethyl]dimethylamine

Using essentially the general procedure described in example 1 and some non-critical variations, the above derivative was prepared. Melting range (° C.): 74-75; IR spectra (cm$^{-1}$): 1180.57 (SO$_2$); Mass (m/z): 441, 443 (M+H)$^+$; $^1$H-NMR (ppm): ☐2.35 (s, 6H); 2.73-2.79 (t, 2H, J=5.4 Hz); 4.04-4.1 (t, 2H, J=5.4 Hz); 6.87 (s, 1H); 7.08-7.12 (d, 2H); 7.40-7.45 (dd, 1H); 7.68-7.83 (m, 4H).

Example-34

[2-(1-(2'-Bromo-4'-methoxybenzenesulfonyl)-5-bromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1150; Mass (m/z): 531, 533, 535 (M+H)$^+$;

Example-35

[2-(1-(2'-Bromo-4'-methylbenzenesulfonyl)-5-bromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1154; Mass (m/z): 515, 517 (M+H)$^+$;

Example-36

[2-(1-(3',4'-Dimethoxybenzenesulfonyl)-5-bromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1154; Mass (m/z): 483, 485 (M+H)$^+$;

Example-37

[2-(1-(4'-Bromobenzenesulfonyl)-5-bromo-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1154; Mass (m/z): 501, 503, 505 (M+H)$^+$;

Example-38

[2-(1-(4'-Chlorobenzenesulfonyl)-5-bromo-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1155; Mass (m/z): 457, 459, 461 (M+H)$^+$;

Example-39

[2-(1-(4'-Methylbenzenesulfonyl)-5-bromo-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1166 (SO$_2$); Mass (m/z): 437, 439 (M+H)$^+$; $^1$H-NMR (ppm): ☐2.35 (s, 3H); 3.01 (s, 6H); 3.65-3.70 (t, 2H, J=5.4 Hz); 4.42-4.47 (t, 2H, J=5.4 Hz); 7.33-7.34 (d, 2H); 7.47-7.81 (d, 5H); 7.91-7.96 (d, 1H).

Example-40

[2-(1-(2'-Bromo-4'-methylbenzenesulfonyl)-5-bromo-2-Methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 329, 531, 533 (M+H)$^+$;

Example-41

[2-(1-(2'-Bromobenzenesulfonyl)-5-bromo-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 515, 517, 519 (M+H)$^+$;

Example-42

[2-(1-(4'-Fluorobenzenesulfonyl)-5-bromo-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 455, 457 (M+H)$^+$;

Example-43

[2-(1-(4'-Fluorobenzenesulfonyl)-5-bromo-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 517, 519 (M+H)$^+$;

Example-44

[2-(1-(4'-Chlorobenzenesulfonyl)-5-bromo-2-phenyl-1H-indol-3-yloxy)ethyl]dimethylamine Using essentially the general procedure described in example 1 and some non-critical variations, the above deriva-

Example-45

[2-(1-(4'-Fluorobenzenesulfonyl)-5,7-dibromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1160 (SO$_2$); Mass (m/z): 519, 521, 523 (M+H)$^+$;

Example-46

[2-(1-(4'-Chlorobenzenesulfonyl)-5,7-dibromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 535, 537, 539 (M+H)$^+$;

Example-47

[2-(1-4'-Fluorobenzenesulfonyl)-5,7-dibromo-2-phenyl-1H-indol-3-yloxy)ethyl]dimethylamine Using essentially the general procedure described in example 1 and some non-critical variations, the above derivative was prepared. Melting range (° C.): Isolated, as oil; IR spectra (cm$^{-1}$): 1166 (SO$_2$); Mass (m/z): 595, 597, 599 (M+H)$^+$;

Example-48

[2-(1-(4'-Methylbenzenesulfonyl)-5,7-dibromo-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1166 (SO$_2$); Mass (m/z): 529, 531, 533 (M+H)$^+$;

Example-49

[2-(1-(4'-Fluorobenzenesulfonyl)-6-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1165; Mass (m/z): 397, 399 (M+H)$^+$; $^1$H-NMR (δ ppm): 2.37 (s, 6H); 2.77-2.83 (t, 2H, J=5.4 Hz); 4.06-4.12 (t, 2H, J=5.4 Hz); 6.86 (s, 1H); 7.06-7.26 (m, 3H); 7.44-7.48 (d, 1H); 7.79-7.86 (m, 2H); 8.00-8.01 (d, 1H).

Example-50

[2-(1-(2'-Bromobenzenesulfonyl)-6-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1160; Mass (m/z): 457, 459, 461 (M+H)$^+$;

Example-51

[2-(1-(4'-Methylbenzenesulfonyl)-6-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1173.4 (SO$_2$); 812, 786 (C—Cl) Mass (m/z): 393, 395 (M+H)$^+$; $^1$H-NMR (δ ppm): 2.35 (s, 9H, CH$_3$ and NMe$_2$); 2.74-2.8 (t, 2H, J=5.4 Hz); 4.05-4.10 (t, 2H, J=5.4 Hz); 6.88 (s, 1H); 7.15-7.26 (m, 3H); 7.42-7.46 (d, 1H); 7.66-7.71 (d, 2H); 8.01-8.02 (d, 1H).

Example-52

[2-(1-Benzenesulfonyl)-6-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 379, 381 (M+H)$^+$; 1H-NMR (δ ppm): 2.34 (s, 6H); 2.72-2.78 (t, 2H, J=5.4 Hz); 4.01-4.10 (t, 2H, J=5.4 Hz); 6.89 (s, 1H); 7.16-7.26 (dd, 1H); 7.38-7.57 (m, 4H); 7.78-7.82 (m, 2H); 8.02-8.03 (d, 1H).

Example-53

[2-(1-(4'-Isopropylbenzenesulfonyl)-6-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 421, 423 (M+H)$^+$;

Example-54

[2-(1-(2'-Bromo-4'-methoxybenzenesulfonyl)-6-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 487, 489, 491 (M+H)$^+$.

Example-55

[2-(1-(2'-Bromo-4'-methylbenzenesulfonyl)-6-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 471, 473, 475 (M+H)$^+$.

Example-56

[2-(1-(3',4'-Dimethoxybenzenesulfonyl)-6-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 439, 441 (M+H)$^+$.

Example-57

[2-(1-(4'-Bromobenzenesulfonyl)-6-chloro-1H-indol-3-yloxy)ethyl]dimethylamine

Using essentially the general procedure described in example 1 and some non-critical variations, the above derivative was prepared.
Melting range (° C.): Isolated as oil; IR spectra (cm$^{-1}$): 1176.21 (SO$_2$); 815, 787 (C—Cl) Mass (m/z): 457, 459, 461 (M+H)$^+$.

Example-58

[2-(1-(4'-Chlorobenzenesulfonyl)-6-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 413, 415, 417 (M+H)$^+$;

Example-59

[2-(1-(4'Fluorobenzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1165; Mass (m/z): 397, 399 (M+H)$^+$; $^1$H-NMR (δ☐☐ ppm): 2.37 (s, 6H); 2.77-2.83 (t, 2H, J=5.4 Hz); 4.06-4.12 (t, 2H, J=5.4 Hz); 6.86 (s, 1H); 7.06-7.26 (m, 3H); 7.44-7.48 (d, 1H); 7.79-7.86 (m, 2H); 8.00-8.01 (d, 1H).

Example-60

[2-(1-(2'Bromobenzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1167; Mass (m/z): 457, 459, 461 (M+H)$^+$;

Example-61

[2-(1-(4'-Methylbenzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1173.4 (SO$_2$); 812, 786 (C—Cl); Mass (m/z): 393, 395 (M+H)$^+$; $^1$H-NMR (δ☐☐ ppm): 2.35 (s, 9H, CH$_3$ and NMe$_2$); 2.74-2.8 (t, 2H, J=5.4 Hz); 4.05-4.10 (t, 2H, J= 5.4 Hz); 6.88 (s, 1H); 7.15-7.26 (m, 3H); 7.42-7.46 (d, 1H); 7.66-7.71 (d, 2H); 8.01-8.02 (d, 1H).

Example-62

[2-(1-(Benzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl) Mass (m/z): 379, 381 (M+H)$^+$; $^1$H-NMR (δ☐☐ ppm): 2.34 (s, 6H); 2.72-2.78 (t, 2H, J=5.4 Hz); 4.01-4.10 (t, 2H, J=5.4 Hz); 6.89 (s, 1H); 7.16-7.26 (dd, 1H); 7.38-7.57 (m, 4H); 7.78-7.82 (m, 2H); 8.02-8.03 (d, 1H).

Example-63

[2-(1-(4'-Isopropylbenzenesulfonyl)-5-Chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 421, 423 (M+H)$^+$.

Example-64

[2-(1-(2'-Bromo-4'-methoxybenzenesulfonyl)-5-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 487, 489, 491 (M+H)$^+$.

Example-65

[2-(1-(2'-Bromo-4'-methylbenzenesulfonyl)-5-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 471, 473, 475 (M+H)$^+$.

Example-66

[2-(1-(3',4'-Dimethoxybenzenesulfonyl)-5-chloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 439 (M+H)$^+$.

Example-67

[2-(1-(4'-Bromobenzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 457, 459, 461 (M+H)$^+$.

Example-68

[2-(1-(4'-Chlorobenzenesulfonyl)-5-chloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 413, 415, 417 (M+H)$^+$.

Example-69

[2-(1-Benzenesulfonyl)-5-chloro-2-phenyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 455, 457 (M+H)$^+$.

Example-70

[2-(1-(2'-Bromo-4'-methylbenzenesulfonyl)-5-chloro-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 547, 549, 551 (M+H)$^+$.

Example-71

[2-(1-(4'-Fluorobenzenesulfonyl)-5-chloro-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 473, 475 (M+H)$^+$.

Example-72

[2-(1-(Benzenesulfonyl)-5-chloro-2-methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 393, 395 (M+H)$^+$.

Example-73

[2-(1-(4-Fluorobenzenesulfonyl)-5-chloro-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 411, 413 (M+H)$^+$.

Example-74

[2-(1-(4'-Fluorobenzenesulfonyl)-5,7-dichloro-1H-Indol-3-yloxy)ethyl]dimethylamine Using essentially the general procedure described in example 1 and some non-critical variations, the above deriva-
tive was prepared. Melting range (° C.): Isolated as oil; IR spectra (cm$^{-1}$): 1176.21 (SO$_2$); 815, 787 (C—Cl); Mass (m/z): 431, 433, 435 (M+H)$^+$.

Example-75

[2-(1-(2'-Bromobenzenesulfonyl)-5,7-dichloro-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 491, 493, 495 (M+H)$^+$.

Example-76

[2-(1-(Benzenesulfonyl)-5,7-dichloro-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 413, 415, 417 (M+H)$^+$.

Example-77

[2-(1-(Benzenesulfonyl)-5,7-dichloro-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 427, 429, 431 (M+H)$^+$.

Example-78

[2-(1-Benzenesulfonyl)-5,7-dichloro-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 489, 491, 493 (M+H)$^+$.

Example-79

[2-(1-(4'Methyl-Benzenesulfonyl)-5,7-Dichloro,2-Phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 503, 505, 507 (M+H)$^+$.

Example-80

[2-(1-(4'-Fluorobenzenesulfonyl)-5-chloro-7-bromo-1H-indol-3-yloxy)ethyl]dimethylamine Using essentially the general procedure described in example 1 and some non-critical variations, the above deriva-

Example-81

[2-(1-(4'-Chlorobenzenesulfonyl)-5-chloro-7-bromo-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 491, 493, 495.

Example-82

[2-(1-Benzenesulfonyl)-5-Chloro-7-bromo-2-methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 471, 473, 475 (M+H)$^+$.

Example-83

[2-(1-(2'-Bromo-4'-methoxybenzenesulfonyl)-5-Chloro-7-Bromo-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 641, 643, 645 (M+H)$^+$.

Example-84

[2-(1-(4'-Fluorobenzenesulfonyl)-5-chloro-7-bromo-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 551, 553, 555 (M+H)$^+$.

Example-85

[2-(1-(4'-Bromobenzenesulfonyl)-5-chloro-7-bromo-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); 815, 787 (C—Cl); Mass (m/z): 611, 613, 615 (M+H)$^+$.

Example-86

[2-(1-Benzenesulfonyl)-5-methoxy-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 375.4 (M+H)$^+$.

Example-87

[2-(1-(4'-Bromobenzenesulfonyl)-5-Methoxy-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$) Mass (m/z): 453, 455 (M+H)$^+$.

Example-88

[2-(1-(4'-Fluorobenzenesulfonyl)-5-Methoxy-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 393.4 (M+H)$^+$.

Example-89

[2-(1-(4'-Chlorobenzenesulfonyl)-5-Methoxy-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 409, 411 (M+H)$^+$.

Example-90

[2-(1-Benzenesulfonyl)-5-Methoxy-2-Methyl-1H-indol-3-yloxy)ethyl]dimethylamine

Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 389.4 (M+H)$^+$.

Example-91

[2-(1-(4'-Fluorobenzenesulfonyl)-5-Methoxy-2-Methyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 407.4 (M+H)$^+$.

Example-92

[2-(1-(4'-Fluorobenzenesulfonyl)-5-methoxy-2-phenyl-1H-indol-3-yloxy)ethyl]dimethylamine Using essentially the general procedure described in example 1 and some non-critical variations, the above derivative was prepared. Melting range (° C.): Isolated as oil; IR spectra (cm$^{-1}$): 1176.21 (SO$_2$); Mass (m/z): 469.5 (M+H)$^+$.

The invention claimed is:
1. A method of treatment of a disorder or medical condition selected from obesity, Alzheimer's, cognition and schizo- phrenia, which comprises administering to a patient a therapeutically effective amount of a compound of general formula (I):

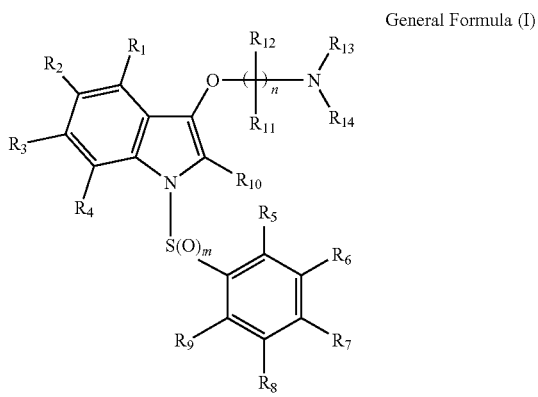
General Formula (I)

its stereoisomers, its radioisotopes, its geometric forms, its N-oxide, its pharmaceutically acceptable salts, wherein $R_1$, $R_2$, $R_3$, $R_4$, $R_5$, $R_6$, $R_7$, $R_8$, $R_9$, may be same or different, and represent hydrogen, halogen, hydroxyl, substituted or unsubstituted groups selected from linear or branched ($C_1$-$C_3$) alkyl and ($C_1$-$C_3$) alkoxy, $R_{10}$ represents hydrogen, halogen, hydroxyl, substituted or unsubstituted groups selected from linear or branched ($C_1$-$C_3$) alkyl and aryl; $R_{11}$, $R_{12}$, $R_{13}$ and $R_{14}$ may be same or different, and represent hydrogen and substituted or unsubstituted groups selected from linear or branched (C1-C3) alkyl; "n" is an integer value representing 2; and "m" is an integer ranging from 0 to 2 and preferably m is 1 or 2.

2. A process for the preparation of a compound of general formula (I)

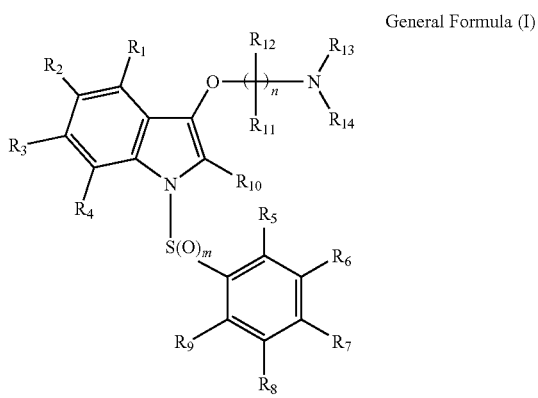
General Formula (I)

its stereoisomers, its radioisotopes, its geometric forms, its N-oxide, its pharmaceutically acceptable salts, wherein $R_1$, $R_2$, $R_3$, $R_4$, $R_5$, $R_6$, $R_7$, $R_8$, $R_9$, may be same or different, and represent hydrogen, halogen, hydroxyl, substituted or unsubstituted groups selected from linear or branched ($C_1$-$C_3$) alkyl and ($C_1$-$C_3$) alkoxy, $R_{10}$ represents hydrogen, halogen, hydroxyl, substituted or unsubstituted groups selected from linear or branched ($C_1$-$C_3$) alkyl and aryl; $R_{11}$, $R_{12}$, $R_{13}$ and $R_{14}$ may be same or different, and represent hydrogen and substituted or unsubstituted groups selected from linear or branched (C1-C3) alkyl; "n" is an integer value representing 2; and "m" is an integer ranging from 0 to 2 and preferably m is 1 or 2; the process comprising:

a) reacting a compound of formula (II),

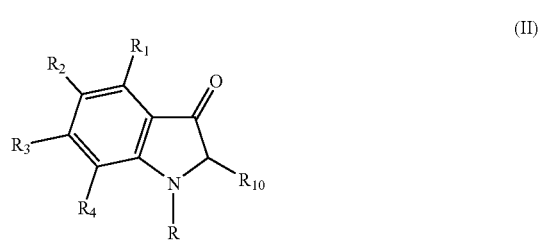
(II)

where R represents either a suitable N-protecting groups or a group such as

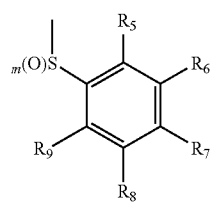

with a compound of formula (III) or its acid addition salt,

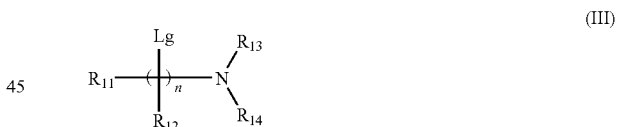
(III)

to obtain compound of general formula (I), wherein Lg is a leaving group.

* * * * *